United States Patent
Terki et al.

(10) Patent No.: US 9,389,285 B2
(45) Date of Patent: Jul. 12, 2016

(54) MICROMAGNETOMETRY DETECTION SYSTEM AND METHOD FOR DETECTING MAGNETIC SIGNATURES OF MAGNETIC MATERIALS

(71) Applicants: Université de Montpellier, Montpellier (FR); CENTRE NATIONAL DE LA RECHERCHE SCIENTIFIQUE (C.N.R.S), Paris (FR)

(72) Inventors: Férial Terki, Le Triadou (FR); Azzedine Bousseksou, Toulouse (FR); Quang Hung Tran, Lyngby (DK); Souleyman Kamara, Montpellier (FR); CheolGi Kim, Daejeon (KR); Kun Woo Kim, Daejeon (KR); Philippe Gandit, Saint-Nizier du Moucherotte (FR)

(73) Assignees: UNIVERSITÉ DE MONTPELLIER, Montpellier (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 19 days.

(21) Appl. No.: 14/414,430

(22) PCT Filed: Jul. 12, 2013

(86) PCT No.: PCT/EP2013/064775
§ 371 (c)(1),
(2) Date: Jan. 12, 2015

(87) PCT Pub. No.: WO2014/009516
PCT Pub. Date: Jan. 16, 2014

(65) Prior Publication Data
US 2015/0168507 A1   Jun. 18, 2015

(30) Foreign Application Priority Data
Jul. 13, 2012  (EP) .................................... 12305852

(51) Int. Cl.
| | |
|---|---|
| *G01R 33/07* | (2006.01) |
| *G01R 33/09* | (2006.01) |
| *B82Y 25/00* | (2011.01) |
| *G01R 33/12* | (2006.01) |

(52) U.S. Cl.
CPC ............... *G01R 33/072* (2013.01); *B82Y 25/00* (2013.01); *G01R 33/091* (2013.01); *G01R 33/096* (2013.01); *G01R 33/1269* (2013.01)

(58) Field of Classification Search
CPC .................... B82Y 25/00; G01V 3/107–3/108
See application file for complete search history.

(56) References Cited

U.S. PATENT DOCUMENTS

| | | | |
|---|---|---|---|
| 6,242,908 B1 * | 6/2001 | Scheller ................... | G01D 3/02  324/207.12 |
| 6,541,965 B1 * | 4/2003 | Binder ................... | G01V 3/104  324/232 |

(Continued)

*Primary Examiner* — Jermele M Hollington
(74) *Attorney, Agent, or Firm* — Knobbe, Martens, Olson & Bear, LLP

(57) ABSTRACT

A micromagnetometry system for detecting the presence of very small quantities of magnetic particles comprises a first magnetic hybrid AMR/PHR multiring sensor using a Wheastone bridge electrical configuration, a first current source, a first voltage measurement device, a set of at least one magnetic particles deposited on the first magnetic sensor and a processing unit for detecting from a set of different measured differential voltages a magnetic flux shift representative of the presence of a least one deposited magnetic particle.

The micromagnetometry system comprises means for creating a magnetic excitation field $H_{AC}$ to make produce by each motionless magnetic particle a stray magnetic field oscillating along the time at a constant frequency ω ranging from 10 Hz to 3 KHz.

27 Claims, 7 Drawing Sheets

(56) References Cited

U.S. PATENT DOCUMENTS

| | | | | |
|---|---|---|---|---|
| 8,354,841 B2 * | 1/2013 | Boeve | ...................... | A61B 5/05 128/899 |
| 8,852,957 B2 * | 10/2014 | Ikeda | ...................... | B82Y 25/00 435/287.2 |
| 9,023,651 B2 * | 5/2015 | Evers | ...................... | B82Y 25/00 436/34 |
| 2002/0135358 A1 * | 9/2002 | Sager | .................. | G01R 33/1215 324/204 |
| 2006/0194327 A1 | 8/2006 | Kahlan et al. | | |
| 2010/0148768 A1 * | 6/2010 | Schwarz | ................ | B82Y 25/00 324/239 |
| 2010/0231213 A1 | 9/2010 | Nieuwenhuis et al. | | |

* cited by examiner

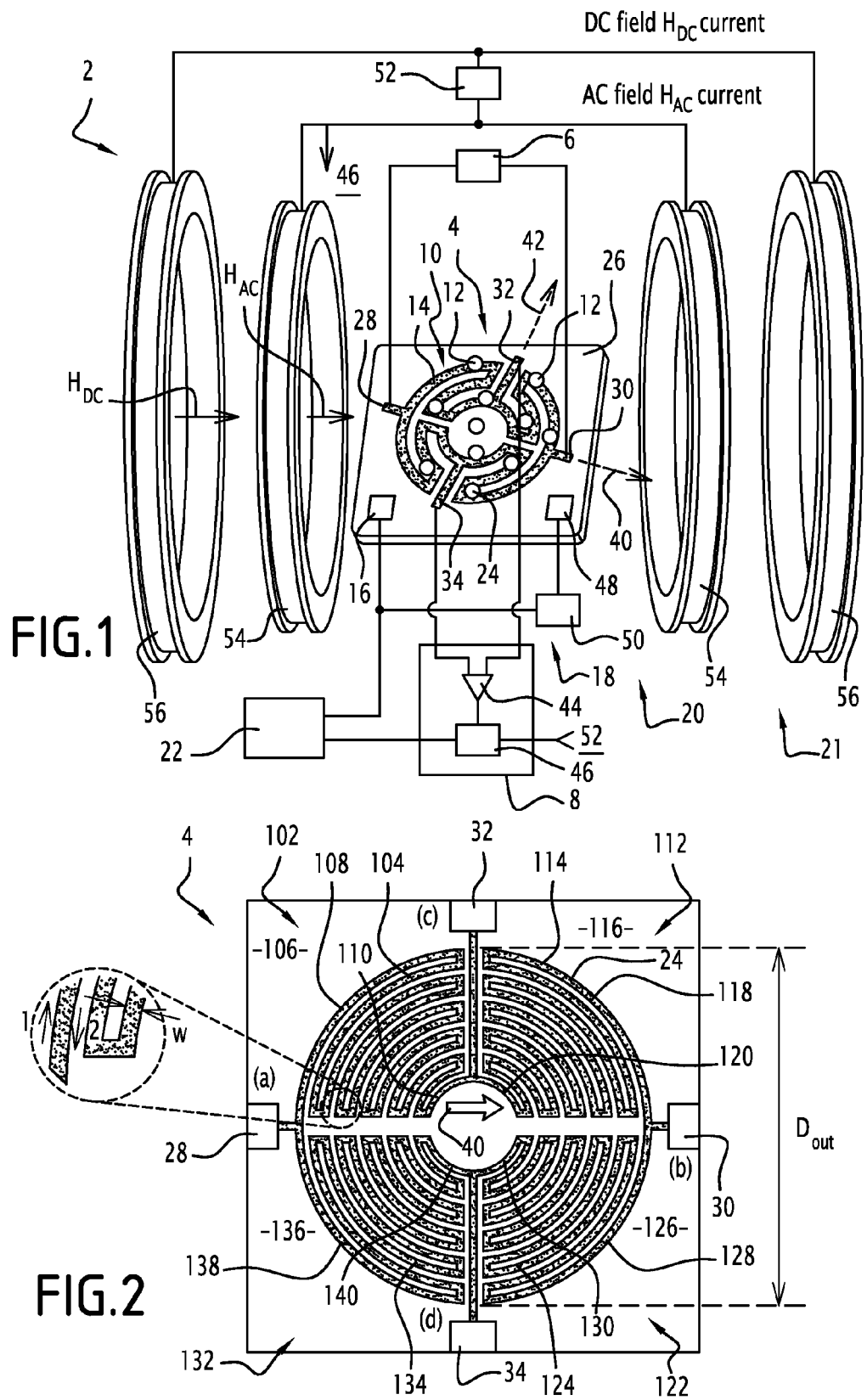

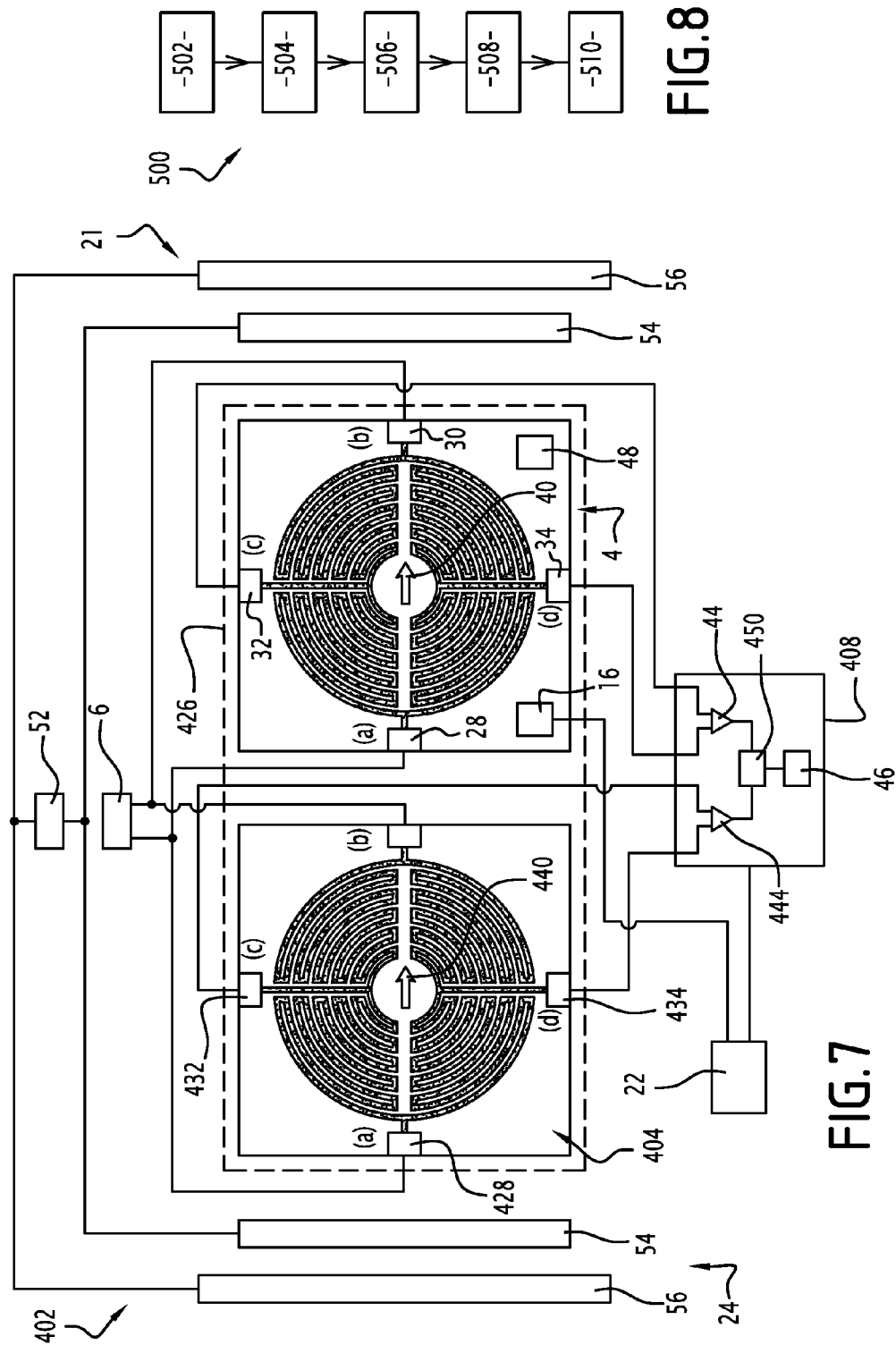

MICROMAGNETOMETRY DETECTION SYSTEM AND METHOD FOR DETECTING MAGNETIC SIGNATURES OF MAGNETIC MATERIALS

FIELD OF THE INVENTION

A micromagnetometry system for detecting the presence of very small quantities of magnetic particles.

BACKGROUND OF THE INVENTION

Nowadays nano-sized Spin CrossOver (SCO) particles receive more and more interests not only for the exploration of the physical properties of these materials at the mesoscopic scale, but also for the development of new functional materials. Up to now observations of the spin transition property was essentially reduced to the simple investigation of temperature dependence of the magnetization or the optical absorption in a huge ensemble of nano-particles with different degrees of size and shape dispersion. The development of methods for single Spin CrossOver (SCO) particle measurements is desirable for both fundamental and applicative perspective even if such efforts remain scare so far.

In the field of nano-scale magnetic measurements, the state of the art is represented by the micro-SQUID and nano-SQUID devices. These devices can detect the magnetization reversal of small amount of magnetic nano-particles or single molecule magnets by depositing directly the nano-particles on the micro-bridge Josephson junctions.

However, for low noise operation, the micro-bridges are normally made of low temperature superconducting materials such as niobium. Such devices are for example described in the article entitled "Magnetic Anisotropy of a Single Cobalt Nanocluster" from M. Jamet and al., published in the Physical Review Letters, Vol. 86, number 20.

Hitherto the working temperature of such a magnetometry detection system is limited below few tens of Kelvin.

Consequently, the conventional micro-SQUID technique is not appropriate to study the magnetization properties within the room temperature range, especially to carry out precise measurements of room temperatures switching properties of a small volume or a single nano-particle of a SCO material.

The current ultra-sensitive SQUID detection method suffers from several drawbacks as being used at very low temperature and requiring complex instruments that are not portable and not flexible.

Alternative methods are proposed as described in the following documents:
- the article from Sunjong Oh et al. untitled "Analytes kinetics in lateral flow membrane analyzed by cTnl monitoring using magnetic method", published in Sensors and Actuators B: Chemical International devoted to Research and Development of Physical and Chemical Transducers, Elsevier S. A., Switzerland, vol. 160, n °1, 19 Aug. 2011, pages 747-752;
- the article from Sunjong Oh et al. untitled "Hybrid AMR/PHR ring sensor", published in Solid State Communications, Pergamon, GB, vol. 151, n °18, 29 May 2011, pages 1248-1251;
- the patent application US 2006/194327 A1;
- the patent application US 2010/231213 A1.

A technical problem is to avoid such disadvantages and to provide an ultra-sensitive magnetometry system that performs measurements at room temperature, which is less complex and offers a more portable and flexible implementation In addition, another technical problem is to propose a magnetometry system and method that improves the sensitivity detection performance in order to detect nano or picotesla field generated by a "single micro/nano object" in the close vicinity of the sensor active surface.

SUMMARY OF THE INVENTION

Accordingly the invention relates to a first micromagnetometry system for detecting the presence of very small quantities of magnetic particles down to a single magnetic particle or a single magnetic object in nano or micro scale comprising a:
- a first magnetic hybrid AMR/PHR multi-ring sensor having an active surface including a magnetic track of a closed loop shape deposited on a substrate, a first current terminal and a second current terminal forming a pair of current terminals which face each other contacting with the closed loop magnetic track made of a magnetic material, a first voltage terminal and a second voltage terminal forming a pair of voltage terminals which face each other contacting with the closed loop magnetic track and from which an output differential voltage $V_b$ is detected, a first axis passing through the first and second current terminals being parallel to the exchange bias field direction of the track material and perpendicular to a second axis passing through the first and second voltage terminals;
- a first current or voltage source connected between the first and second current terminals for injecting a current I therethrough;
- a first voltage measurement device connected between the first and second voltage terminals for measuring the differential voltage $V_b$ between the pair of voltage terminals;
- a set of at least one magnetic particles deposited on the active surface of the first magnetic sensor;
- a processing unit for detecting from a set of different measured differential voltages a magnetic flux shift representative of the presence of a least one deposited magnetic particle;

the magnetic track of the first AMR/PHR multi-ring magnetic sensor having:
- a first arm made of a first set of a predetermined ring number m lower than 18 of circular meander paths delimited within a first quarter surface of the first magnetic sensor, the outermost meander path being connected to the first current terminal and the innermost meander path being connected to the first voltage terminal,
- a second arm made of a second set of the same predetermined number m of circular meander paths delimited within a second quarter surface of the first magnetic sensor, the outermost meander path being connected to the second current terminal and the innermost meander path being connected to the first voltage terminal,
- a third arm made of a third set of the same ring number m of circular meander paths delimited within a third quarter surface of the first magnetic sensor, the outermost meander path being connected to the second current terminal and the innermost meander path being connected to the second voltage terminal,
- a fourth arm made of a fourth set of the same ring number m of circular meander paths delimited within a fourth quarter surface of the first magnetic sensor, the outermost meander path being connected to the first current terminal and the innermost meander path being connected to the second voltage terminal;

the magnetic track is a bi-layered structure including a ferromagnetic film and an anti-ferromagnetic films, or a spin-valve structure, or a tri-layered structure including a ferromagnetic film, a metal and an anti-ferromagnetic film;

characterized in that the micromagnetometry system comprises means for creating a magnetic excitation field $H_{AC}$ to make produce by each magnetic particle a stray magnetic field, the magnetic excitation field $H_{AC}$ oscillating along the time at a constant frequency ω ranging from 10 to 3 KHz; and the magnetic particles to be detected are motionless and placed close to or in contact with the active surface of the magnetic track; and the current I injected by the first current or voltage source passing through the current terminals is a direct current (DC), or an alternating current (AC), or a sum of a direct and an alternating current; and the processing unit is configured to either provide with a first calibration curve of a background thermal magnetic response of the first magnetic sensor without any magnetic particles deposited thereon, over a predetermined temperature range, under first known predetermined environmental physical conditions, and under a first set of known system operating conditions in terms of the injected current by the first current or voltage source and of the magnetic excitation field $H_{AC}$ applied; then after deposit of an unknown amount of magnetic particles upon the first magnetic sensor, determining a second curve of the evolution versus temperature of differential voltage measurements corrected or not from a set of differential voltage measurements output from the first magnetic sensor and carried out by varying the temperature over the same predetermined range of temperature, under the same first known predetermined environmental physical conditions and under the same first set of known system operating conditions, then to determine a third curve as the difference the second curve and the first curve over the same range of temperature; and to detect the presence of at least one magnetic particle when the absolute value of all the voltage differences of the third curve remains above a predetermined detection threshold or when the third curve exhibits a temperature interval over which a transition occurs having an amplitude greater than the predetermined detection threshold, the predetermined detection threshold corresponding to a minimal magnetization field shift detectable of 10 nT;

either, after deposit of an unknown amount of magnetic particles upon the first magnetic sensor, the magnetic particles being switchable molecular nanoparticles by overstepping a predetermined switching threshold in terms of a switching physical property that operates as a switching command, by varying the physical property magnitude over a predetermined range of the physical property under known predetermined physical conditions and under known system operating conditions, to determine a first curve of the evolution of differential voltage measurements corrected or not from the evolution of differential voltage measurements carried out by the first magnetic sensor versus the magnitude of the physical property; then to determine over the predetermined range of the physical property magnitude a second curve as a fitting curve from a lower portion of the first curve, this lower portion of the first curve corresponding to a lower interval included within the predetermined range of the physical property, the lower interval having its upper bound lower than the predetermined switching threshold; then to determine a third curve as the difference versus the magnitude of the switching physical property between the differential voltages of the first curve and the differential voltages of the second curve within the same range of magnitude of the physical property; and to detect the presence of magnetic particles when the third curve exhibits a switching physical property interval over which a transition occurs having an amplitude greater than the predetermined detection threshold, the predetermined detection threshold corresponding to a minimal magnetization field shift detectable of 10 nT.

According to particular embodiments, the micromagnetometry system comprises at least one of the following features:

a first environmental temperature sensor for measuring an environmental temperature and/or a second environmental sensor for measuring a physical property different from the environmental temperature placed close to the active surface of the first active sensor, the switching of a magnetization of the magnetic particles being actuated when temperature or the physical property different of temperature is above or below a predetermined switching threshold, means for controlling and/or regulating the environmental temperature and/or the physical environmental property different from the temperature, the means for creating a magnetic excitation field $H_{AC}$ comprises a second current source supplying an AC current and a least one coil connected to the second AC current source, the at least one coil being positioned relative to the first magnetic sensor so that the magnetic excitation field $H_{AC}$ has a main component collinear to the first axis, means for creating a magnetic sensor bias field $H_{DC}$ to shift the operating point of the first magnetic sensor to a highest sensing region, the magnetic sensor bias field $H_{DC}$ being constant along the time, and being collinear with the magnetic excitation field $H_{AC}$ created by means for creating a magnetic excitation field $H_{AC}$, wherein the angle α formed between the first axis passing through the first and second current terminals and the axis of magnetic sensor bias field $H_{DC}$ is selected in the range [0 degree, 90 degrees] so that the sensitivity of the magnetic sensor is maximal, and preferably is comprised within the range [15 degrees, 25 degree], the means for creating a magnetic excitation field $H_{AC}$ is the current or voltage source connected between the first and second current terminals, the current or voltage source being configured to generate an alternating current (AC) oscillating along the with time at a constant frequency ω ranging from 10 Hz to 3 KHz, preferably ranging from 50 Hz to 150 Hz, comprising further a second magnetic hybrid AMR/PHR multi-ring sensor having the same structure as the first magnetic hybrid AMR/PHR multi-ring sensor, the first and the second magnetic hybrid AMR/PHR multi-ring sensors being placed close to each other on the same substrate under the same known physical conditions to measure the same magnetic field when no magnetic particles are deposited onto the sensors, the second magnetic hybrid AMR/PHR multi-ring sensors having a first current terminal and a second current terminal forming a pair of current terminals connected in parallel to and sharing the same first current source of the first magnetic hybrid AMR/PHR multi-ring sensor; and wherein the micromagnetometry system is configured to differentiate a first set of differential voltage measurements carried out by the first sensor corresponding to a first configuration wherein magnetic particles to be detected if they are contained in the solution dropped are deposited on the first magnetic sensor and placed under a set of known environmental conditions and system operating settings, and a second set of reference differential voltage measurements carried out by the second sensor corresponding to a second configuration wherein no magnetic particles are deposited thereon, under the same set of known environmental physical conditions and system operating settings and to provide a corresponding difference curve; and then to detect from the difference curve an abrupt variation corresponding at least to a minimal magnetization field shift of 10 nT.

The invention also relates to a second micromagnetometry system for detecting the presence of very small quantities of magnetic particles down to a single magnetic particle or a single magnetic object in nano or micro scale comprising:

a first magnetic hybrid AMR/PHR sensor and a second magnetic hybrid AMR/PHR multi-ring sensor, the first magnetic hybrid AMR/PHR sensor having a first active surface including a first magnetic track deposited on a substrate, a first current terminal and a second current terminal forming a pair of current terminals which face each other contacting with the first magnetic track made of a magnetic material, a first voltage terminal and a second voltage terminal forming a pair of voltage terminals which face each other contacting with the first magnetic track and from which an output differential voltage is detected, a first axis passing through the first and second current terminals being parallel to the exchange bias field direction of the track material and perpendicular to a second axis passing through the first and second voltage terminals;

characterized in that the micromagnetometry system comprises a second magnetic hybrid AMR/PHR sensor being placed close to the second magnetic hybrid AMR/PHR sensor on the same substrate under the same known physical conditions to measure the same magnetic field when no magnetic particles are deposited onto the sensors, the second magnetic hybrid AMR/PHR multi-ring sensor having a second active surface including a second magnetic track deposited on the same substrate, a first current terminal and a second current terminal forming a pair of current terminals which face each other contacting with the second magnetic track made of a magnetic material, a first voltage terminal and a second voltage terminal forming a pair of voltage terminals which face each other contacting with the second magnetic track and from which an output differential voltage is detected, a first axis passing through the first and second current terminals being parallel to the exchange bias field direction of the track material and perpendicular to a second axis passing through the first and second voltage terminals, the first and the second magnetic tracks having a same shape amongst a cross shape, a single ring closed loop shape and a multi-ring closed loop shape, and having a same layer structure, the layer structure of the first and the second magnetic tracks being a bi-layered structure including a ferromagnetic film and an anti-ferromagnetic films, or a spin-valve structure, or a tri-layered structure including a ferromagnetic film, a metal and an anti-ferromagnetic film;

and in that the micromagnetometry system comprises:

a same first current or voltage source connected to and supplying in parallel a current I to the first magnetic hybrid AMR/PHR sensor and the second magnetic hybrid AMR/PHR multi-ring sensor, a first voltage measurement device connected at its input to the first and second voltage terminals of the first magnetic hybrid AMR/PHR sensor and the second magnetic hybrid AMR/PHR sensor, and configured to determine the difference voltage between an amplified differential voltage detected at the voltage terminals of the first magnetic sensor and an amplified differential voltage detected at the voltage terminals of the second magnetic sensor;

a set of at least one magnetic particles deposited on the active surface of the first magnetic sensor;

a processing unit for detecting from a set of different measured differential voltages output by first voltage measurement device a magnetic flux shift representative of the presence of a least one magnetic particle deposited on the first magnetic sensor;

means for creating a magnetic excitation field $H_{AC}$ to make produce by each magnetic particle a stray magnetic field, the magnetic excitation field $H_{AC}$ oscillating along the time at a constant frequency $\omega$ ranging from 10 to 3 KHz; and in that the magnetic particles or the magnetic object to be detected are motionless and placed only close to or in contact with the active surface of the first magnetic track; and the current I injected by the first current or voltage source passing through the current terminals is a direct current (DC), or an alternating current (AC), or a sum of a direct and an alternating current.

According to a particular of embodiment of the second micromagnetometry system, wherein no magnetic particles or magnetic object in nano or micro scale are deposited on the second sensor, and the processing unit is configured to after deposit of an unknown amount of magnetic particles or a magnetic object upon the first magnetic sensor, either under known predetermined physical conditions, to detect the presence of magnetic particles or a magnetic object when a second difference as the difference between a first difference and a reference difference has an amplitude greater than a predetermined detection threshold, the reference difference being the difference between a first voltage measurement carried out by the first sensor that has no magnetic particles thereon and a second voltage measurement carried out by the second sensor that has no magnetic particles thereon under the same known predetermined physical conditions, the first difference being determined by the first voltage measurement device as the difference between the first voltage measurement carried out by the first sensor that has magnetic particles thereon and the second voltage measurement carried out by the second sensor that has no magnetic particles thereon, and the predetermined detection threshold corresponding to a minimal magnetization field shift detectable of 10 nT, either when the magnetic particles are molecular nanoparticles or a magnetic object switchable by overstepping a predetermined switching threshold in terms of a switching physical property that operates as a switching command, under known predetermined physical conditions, by varying the physical property magnitude over a predetermined range of the physical property, to determine a curve as the evolution versus the physical property magnitude of the difference between a first set of differential voltage measurements and a second set of voltage measurements, the first set of voltage measurements being carried out by the first sensor that has magnetic particles thereon and the second set of voltage measurements carried out by the second sensor that has no magnetic particles thereon, and then to detect the presence of magnetic particles or magnetic object when the curve exhibits a switching physical property interval over which a transition occurs having an amplitude greater than the predetermined detection threshold, the predetermined detection threshold corresponding to a minimal magnetization field shift detectable of 10 nT.

According to particular embodiments of the first and second micromagnetometry systems, wherein the magnetic particles are comprised in the family of:

Any switchable molecular nanoparticles in form of $A_hB_k[M(CN)_6]_l \cdot mH_2O$, where A can be Co, Ni, Fe, etc, B and M can be various transition metals ($Fe^{II}$, $Fe^{III}$, $Mn^{II}$, $Mn^{III}$, fm1 a$Co^{II}$, $Co^{III}$, ...) and C is an alkali metal cation;

Any paramagnetic particles: $Fe_2O_3$, $Fe_3O_4$, $Fe@Fe_3O_4$, $CoFe@Fe_3O_4$, Ni, ...;

Any ferromagnetic particles: Fe, CoFe, Ni;

Any antiferromagnetic particles;

Any particles with multilayer structure Ti/Fe, Cr, NiO, $Co_3O_4$, a-$Fe_2O_3$, CuO, MnO, $Cr_2O_3$ nanoparticles;

Any magnetic bead made of $Fe_3O_4$ in the polymer matrix with the sphere shape and any size ranging from 50 nm to 10 µm.

The invention also relates to a first detection method for detecting the presence of very small quantities of magnetic particles carried out by a micromagnetometry system, comprising the following steps of firstly, calibrating in temperature under first known predetermined physical conditions the first magnetic sensor when the system comprises a single first magnetic sensor, or the set of the first and second magnetic sensor when the magnetometry system comprises a first magnetic sensor and a second magnetic sensor by providing a first calibration background thermal noise curve; then deposit an unknown amount of magnetic particles upon the first magnetic sensor; then, under the same first known predetermined physical conditions, by varying temperature on a predetermined range of temperature, when the magnetometry system comprises a first single magnetic sensor, outputting a second curve as the evolution of differential voltage measurements carried out by the first sensor versus temperature, or when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a second curve as the evolution versus temperature of the difference between the first set of differential voltage measurements and the second set of differential voltage measurements;

determining a third curve as the difference versus temperature between the differential voltages of the second curve and the differential voltages of the first curve within the same range of temperature; and detecting the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

The invention also relates to a second detection method for detecting the presence of very small quantities of magnetic particles carried out by a micromagnetometry system, comprising the following steps of depositing an unknown amount of magnetic particles upon the first magnetic sensor, the magnetic particles being switchable molecular nanoparticles by overstepping a predetermined switching threshold in terms of a switching physical property that operates as a switching command, then in a next step, under known predetermined physical conditions, by varying the physical property magnitude over a predetermined range of the physical property, when the magnetometry system comprises a first single magnetic sensor, outputting a first curve as the evolution of differential voltage measurements carried out by the first sensor versus the magnitude of the physical property, or when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a first curve as the evolution versus the physical property of the difference between the first set of differential voltage measurements and the second set of differential voltage measurements; then determining over the predetermined range of the physical property a second curve as a fitting curve from a lower portion of the first curve, this lower portion of the first curve corresponding to a lower interval included within the predetermined range of the physical property having its upper bound lower than the predetermined switching threshold;

determining a third curve as the difference versus the magnitude of the switching physical property between the differential voltages of the first curve and the differential voltages of the second curve within the same range of magnitude of the physical property; and detecting the presence of magnetic particles when the third curve exhibits a switching physical property interval over which a transition occurs having an amplitude greater than the predetermined detection threshold, the predetermined detection threshold corresponding to a minimal magnetization field shift detectable of 10 nT.

According to particular embodiments, in the second detecting method for detecting the presence of very small quantities of magnetic particles, the switching physical property is temperature, pressure, optical irradiation, electrical field, magnetic field, chemical guest molecules.

The invention also relates to a third detection method for detecting the presence of very small quantities of magnetic particles down to a single magnetic particle or a single magnetic object in nano or micro scale carried out by a micromagnetometry system, comprising the following steps of depositing an unknown amount of magnetic particles or a single magnetic object upon the first magnetic sensor, then either under known predetermined physical conditions, outputting a first voltage measurement carried out by the first sensor that has magnetic particles thereon and a second voltage measurement carried out by the second sensor that has no magnetic particles thereon, and determining a first difference between the first voltage measurement and the second voltage measurement; then detecting the presence of magnetic particles or a magnetic object when a second difference as the difference between the first difference and a reference difference has an amplitude greater than a predetermined detection threshold, the reference difference being the difference between a first voltage measurement carried out by the first sensor that has no magnetic particles thereon and a second voltage measurement carried out by the second sensor that has no magnetic particles thereon under the same known predetermined physical conditions, and the predetermined detection threshold corresponding to a minimal magnetization field shift detectable of 10 nT, either when the magnetic particles are molecular nanoparticles or a single object switchable by overstepping a predetermined switching threshold in terms of a switching physical property that operates as a switching command, under known predetermined physical conditions, by varying the physical property magnitude over a predetermined range of the physical property, then outputting a first set of voltage measurements carried out by the first sensor that has magnetic particles thereon and a second set of voltage measurements carried out by the second sensor that has no magnetic particles thereon, and determining a curve as the evolution versus the physical property magnitude of the difference between the first set of differential voltage measurements and the second set of voltage measurements; then detecting the presence of magnetic particles or magnetic object when the curve exhibits a switching physical property interval over which a transition occurs having an amplitude greater than the predetermined detection threshold, the predetermined detection threshold corresponding to a minimal magnetization field shift detectable of 10 nT, The invention also relates to a humidity or gas sensing measurement system comprising a micromagnetometry system, wherein the particles are molecular nanoparticles are switchable by overstepping a predetermined temperature switching threshold, the predetermined temperature switching threshold depending on the humidity of the degree environment, or on the environment concentration of any vapour of external molecules, and wherein the processing unit is configured to determine the humidity degree or the environment concentration of the vapour of external molecules from magnetic field change measurements of magnetic particles that are sensitive to the humidity degree or the environment concentration of the vapour of external molecules, and from a previously determined mapping curve between a calibrated humidity degree or a calibrated environment concentration of the vapour of external molecules measured by another method and a corresponding parameter such as a temperature threshold, a transition temperature, or a width of an hysterisis loop determined through the magnetic property change of the magnetic particles detected by the micromagnetometry method as defined hereabove.

According to a particular embodiment, in the humidity or gas sensing measurement system, the vapour of external molecules that can be detected are amongst the external molecules of the family consisting of $N_2$, He, $I_2$, $CO_2$, ethanol, methanol, 2-propanol, acetone, $D_2O$, $CS_2$, CO, Iode (I), brome (Br), chlore (Cl), benzene, toluene, chlorobenzene, bromobenzene, iodobenzene, dichlorobenzene, trichlorobenzene, pyrazine, pyridine, pyrrole, thiophene, furane, thf.

BRIEF DESCRIPTION OF THE DRAWINGS

A better understanding of the invention will be facilitated by reading the following description, which is given solely by way of examples and with reference to drawings in which:

FIG. 1 is a view of the architecture of a micromagnetometry system according to a first embodiment of the invention wherein an exciting magnetic field $H_{AC}$ is generated by means external to the sensor;

FIG. 2 is a planar detailed view of the hybrid AMR/PHR multi-ring magnetic sensor used by the micromagnetometry system of FIG. 1;

FIG. 7 is a view of the architecture of a micromagnetometry system according to a third embodiment of the invention wherein a second magnetic sensor has been added as a calibrating magnetic sensor;

FIG. 8 is an example of a flow diagram of a micromagnetometry detection method according a first embodiment of the invention, the method being carried out when magnetic particles are switchable molecular nanoparticles by overstepping a predetermined switching threshold in terms of a switching physical property that operates as a switching command;

DETAILED DESCRIPTION OF THE PREFERRED EMBODIMENT

Figure 3:
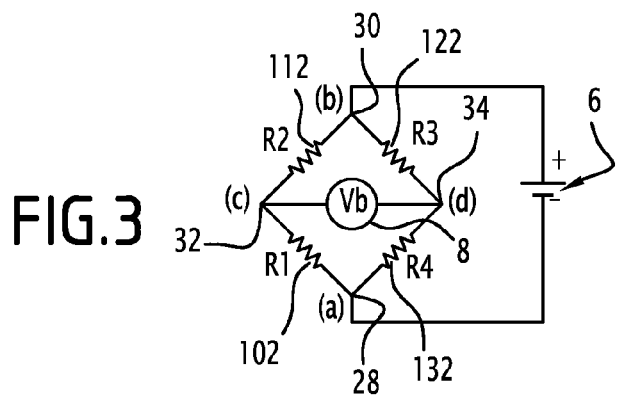
FIG. 3 is an electrical schematic view of the hybrid AMR/PHR multi-ring magnetic sensor of FIG. 2.

According to FIG. 1, a micromagnetometry system 2 for detecting the presence of very small quantities of magnetic particles comprises a first magnetic hybrid Anisotropic Magneto-Resistive AMR/Planar Hall Resistive PHR multi-ring magnetic sensor 4, a first current or voltage source 6, a first voltage measurement device 8, a set 10 of at least one magnetic particles 12 deposited on an active surface 14 of the first magnetic sensor 4, a first environmental temperature sensor 16, means 18 for controlling and/or regulating the environmental temperature of the magnetic particles, means 20 for creating a magnetic alternating excitation field $H_{AC}$ to produce by each magnetic particle a stray magnetic field, means 21 for creating a magnetic sensor bias field $H_{DC}$, and a processing unit 22.

The first magnetic hybrid AMR/PHR multi-ring magnetic sensor 4 or first magnetic sensor includes on its active surface 14 a magnetic track 24 of a closed loop shape deposited on a substrate 26.

The first magnetic sensor 4 has a first current terminal 28 and a second current terminal 30 forming a pair of current terminals which face each other contacting with the closed loop magnetic track 24.

The first magnetic sensor 4 has a first voltage terminal 32 and a second voltage terminal 34 forming a pair of voltage terminals which face each other contacting with the closed loop magnetic track 24 and from which an output differential voltage is detected.

The first magnetic sensor 4 has a first axis 40 or easy axis passing through the first and second current terminals 28, 30 being parallel to the exchange bias field direction of the material and perpendicular to a second axis 42 passing through the first and second voltage terminals 32, 34.

The first current or voltage source 6, connected between the first and second current terminals, is configured to inject a DC bias current I for the first magnetic sensor 4 through the pair of the first and second current terminals 28, 30. The first current source 6 is for example a Keithley 2400 current source and the amplitude of the DC bias current is set equal to 1 mA.

The first voltage measurement device 8 is connected between the first and second voltage terminals 32, 34 for measuring a differential voltage $V_b$ between the pair of voltage terminals 32, 34.

The first voltage measurement device 8 comprises a low noise amplifier 44 with a gain of 20 dB for amplifying the detected differential voltage and driving the output signal obtained to a synchronizing amplifying device 46 based on a phase lock loop. The synchronizing amplifier is configured to lock the measured differential voltage signal onto the magnetic alternating excitation field signal and to detect the peak measured differential voltage measured at the output of the pair of voltage terminals 32, 34.

The first environmental temperature sensor 16 is configured to measure a temperature representative of the actual environmental temperature T of the magnetic particles 12 and the first magnetic sensor 4, and is preferably located close to the active surface 14 of the first magnetic sensor 4. For instance, the environmental temperature sensor 16 is a platinum resistance of 100 Ohms.

The means 18 for controlling and/or regulating the temperature T are configured to heat by a heater 48 in a controlled way the environment of the magnetic particles 12 and are preferably located close to the active surface 14 of the first magnetic sensor 4. The heater 48 is for instance a resistance Minco attached to the first magnetic sensor 4 and connected to a Lakeshore 332 temperature controller 50 that controls the environmental temperature T variation by varying the temperature T from 300 K to 350 K.

The means 20 for creating an alternating magnetic excitation field $H_{AC}$ is configured to make produce by each magnetic particle 12 a stray magnetic field oscillating along the time at a constant frequency ω ranging from 10 to 3 KHz, here set to 100 Hz.

The means 20 for creating the alternating magnetic excitation field $H_{AC}$ comprises here a second current source 52 supplying a AC current oscillating at the frequency of 100 Hz, and at least one coil, here two Helmholtz coils 54, connected to the second AC current source 52.

The two Helmholtz coils 54 are positioned relative to the first magnetic sensor 4 so that a main component of the magnetic excitation field $H_{AC}$ is collinear with the first axis 40.

The means 20 for creating an alternating magnetic sensor bias field $H_{DC}$ is configured to shift the operating point of the first magnetic sensor 4 to a highest sensitivity region, the magnetic sensor bias field $H_{DC}$ being constant along the time, and being collinear with the alternating magnetic excitation field $H_{AC}$.

The bias angle α formed between the first axis 40 passing through the first and second current terminals and the axis of the magnetic sensor bias field $H_{DC}$ is selected in the range of [0 degree, 90 degree] so that the sensitivity S of the first magnetic sensor 4 is maximal. Here, this angle α equals to 20 degrees.

Whole the first magnetic sensor 4 and subsequently all the magnetic particles 12 deposited thereon are thus placed under an hybrid alternative and continuous magnetic field ($H_{AC}$+ $H_{DC}$) the direction thereof forms an angle of 20 degree with the easy axis 40 of the first magnetic sensor 4.

With the combination of both $H_{AC}$ and $H_{DC}$ field, the sensitivity S of the first magnetic sensor 4 is enhanced.

Here, $H_{DC}$ shifts the operating point of the magnetic sensor 4 to the highest sensitivity region, the optimized magnitude of the magnetic field being equal here to 1.4 mT.

The field $H_{AC}$ introduced to generate the stray field of the SCO nano-particles 12 equals here to 0.5 mT in rms value at the frequency of 100 Hz.

The set 10 of the at least one magnetic particles 12 are deposited on the surface of the magnetic sensor.

Here, the magnetic particles 12 are [Fe(hptrz)$_3$](OTs)$_2$ Spin-Crossover nanoparticles elaborated in an homogenous solution of chloroform. They are directly dropped on the whole active surface 14 of the first magnetic sensor.

The magnetic particles 12 to be detected are thus motionless and placed close to or in contact with the active surface 14 of the first magnetic sensor 4.

These magnetic SCO nanoparticles 12 exhibit a magnetic signature corresponding to the diamagnetic to paramagnetic transition wherein the transition temperatures or switching temperatures under open air with a predetermined degree of humidity are $T_{1/2\downarrow}$ equal to 325 K and $T_{1/2\uparrow}$ equal to 331 K while cooling and heating respectively.

These transition temperatures have been verified by an optical reflectance change test that shows the same values under the same humidity conditions.

The processing unit 22 is configured for detecting from a set of different differential voltages measured by the first voltage measurement device 8 a magnetic flux shift representative of the presence of at least one deposited magnetic particle 12 on the active surface 14 of the first magnetic sensor 4.

The magnetic particles 12 are assumed here to be molecular nanoparticles switchable in terms of a transition between two magnetic states when overstepping a predetermined temperature switching threshold, the temperature operating as a switching or actuating command.

The processing unit 22 is configured to, after the deposit of an unknown amount of magnetic particles 12 upon the first magnetic sensor 22 and after varying the temperature T over the predetermined temperature range, determine a first curve of the evolution versus temperature of the differential voltage measurements outputted by the first voltage measurement device 8 and carried out under the known environmental physical conditions and operating system settings.

The processing unit 22 is configured to subsequently determine over the predetermined range of temperature a second curve as a fitting curve from a lower portion of the first curve, this lower portion of the first curve corresponding to a lower interval included within the predetermined range of temperature, the lower interval having its upper bound lower than the temperature switching threshold.

The processing unit 22 is configured to, subsequently determine a third curve as the difference versus the temperature of the differential voltages of the first curve and the differential voltages of the second curve within the same range temperatures, namely [300K, 350K].

The processing unit 22 is configured to subsequently detect the presence of at least one magnetic particle when the third curve exhibits a temperature interval wherein a voltage transition occurs and when the amplitude of this transition is greater than a predetermined detection threshold, the predetermined detection threshold corresponding to a minimal magnetization field shift detectable of 10 nT.

As a variant, the micromagnetometry system comprises a second sensor for measuring a physical property different from temperature, placed close to the active surface of the active sensor, the switching of a magnetization of the magnetic particles between two magnetization states being actuated when the physical property different from temperature is above or below a predetermined switching threshold.

As a variant, the micromagnetometry system comprises second means for controlling and/or regulating a physical environmental property different from temperature, placed preferably close to the active surface of the active sensor.

As a variant, the processing unit is configured to provide of a first calibration background thermal noise curve by calibrating in temperature under first known predetermined physical conditions the first magnetic sensor that has no magnetic particles thereon.

The processing unit is configured to after deposit of an unknown amount of magnetic particles upon the first magnetic sensor, by varying temperature on a predetermined range of temperature under the same first known predetermined physical conditions, to subsequently determine a second curve of the evolution versus temperature of differential voltage measurements corrected or not from the evolution of differential voltage measurements carried out by the first magnetic sensor.

The processing unit is configured to subsequently determine a third curve as the difference versus temperature between the differential voltages of the second curve and the differential voltages of the first curve within the same range of temperature.

The processing unit is configured to detect the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

According to FIG. 2, the first magnetic sensor 4 is based on a multi-ring architecture and is manufactured using a lithography technique in a clean-room of class 1000 with a lift-off process.

Here, the magnetic track 24 is a tri-layered material, for example Ta(3)/NiFe(20)/Cu(0.2)/IrMn(10)/Ta(3) (nm). In this structure, the soft magnetic layer NiFe is the sensing material that is weakly coupled to an anti-ferromagnetic layer (IrMn) by a long range exchange bias field through a few atomic Cu layer.

The tri-layer structure Ta(3)/NiFe(20)/Cu(0.2)/IrMn(10)/Ta(3) nm is deposited by a 6 gun-magnetron sputtering system with a based vacuum of about $10^{-8}$ Torr.

To prevent the contamination, the magnetic sensor is passivated by a $Si_2O_3/Si_3N_4$ bi-layer with a nominal thickness of 200 nanometers.

The outer diameter of the first magnetic sensor 4 is equal here to 300 μm and the width w of the magnetic track 24 is equal to 10 μm.

The magnetic track 24 of the first magnetic sensor 4 has:
a first arm 102 made of a first set of a predetermined ring number m of circular meander paths 104 delimited within a first quarter surface 126 of the magnetic sensor 4, the outermost meander path 128 being connected to the first current terminal 30 and the innermost meander path 110 being connected to the first voltage terminal 32,
a second arm 112 made of a second set of the same predetermined number m of circular meander paths 114 delimited within a second quarter surface 116 of the magnetic sensor 4, the outermost meander path 118 being connected to the second current terminal 30 and the innermost meander path 120 being connected to the first voltage terminal 32,
a third arm 122 made of a third set of the same ring number m of circular meander paths 124 delimited within a third quarter surface 126 of the magnetic sensor 4, the outermost meander path 128 being connected to the second current terminal 30 and the innermost meander path 130 being connected to the second voltage terminal 34,
a fourth arm made 132 of a fourth set of the same ring number m of circular meander paths 134 delimited within a fourth quarter surface 136 of the magnetic sensor 4, the outermost meander path 138 being connected to the first current terminal 30 and the innermost meander path 140 being connected to the second voltage terminal 34.

This multi-ring architecture enhances the sensitivity of the magnetic sensor in a compact region.

As the length of the arms increases with the ring number, filling the sensing meander paths enhances the active sensing area.

The current direction alternately changes for successive ring paths, i.e. there is a current angle range $\theta=\pi/2$ to 0 for path 1 shown in the inset of FIG. 2, and $\theta=\pi$ to $3\pi/2$ for path 2 in the inset of FIG. 2. The sign of the calculated value for path 1 and 2 is the same, which means that AMR effect for both currents is additive. Thus, the maximum voltage variation in the profiles and accordingly the field sensitivity of the arm resistance increases the ring number.

The voltage profile for the full magnetic ring, that is the sum of the AMR and PHR effects, reveals anti-symmetric behavior with the applied field due to self-balancing of ring arm resistances, where the voltage variations are additive for all junction components.

The sensitivity of first magnetic sensor is enhanced by using a tri-layer structure which has a small exchange coupling field and high active current.

This multi-ring architecture enhances the field sensitivity and the active area of the magnetic sensor.

Thus, the first magnetic sensor is a highly sensitive hybrid magneto-resistive (MR) sensor combining Anisotropic Magneto Resistive (AMR) and Planar Hall Effect (PSE) that is capable to detect the switching of the spin states of SCO nano-particles.

Preferably the ring number m of circular meander paths is comprised between 9 and 13. Here, each arm has eleven meander paths or quarters of circular rings, this number maximizing the sensitivity of the first magnetic sensor 4.

This multilayer stack exhibits a very high sensitivity of about S=15 volts/T$^{-1}$ and a low white noise of about 1 nV.Hz$^{-1/2}$ at 100 Hz.

According to the electrical scheme of FIG. 3, the multi-ring geometry of the track and the connectivity of the four arms lead to a Wheastone bridge configuration.

The output voltage of first the magnetic sensor is known as the planar effect Hall effect and is given the equation:

$$V_{PHE} = V_0 \sin\theta \cdot \cos\theta$$

Where $V_0$ depends upon the structure parameter of the sensor such as parallel resistivity $\rho_{//}$ and perpendicular resistivity $\rho_\perp$ relative to magnetization of the sensor, the thickness t of the sensor, and the size of the sensor, $\theta$ is the angle between the direction of the actual magnetization and the applied magnetic field.

The ring architecture advantageously provides with high sensing performance due to the Wheastone bridge electrical configuration.

In the general case, the differential voltage $V_b$ detected between the first voltage V1 of the first voltage terminal and the second voltage V2 of the second voltage terminal is described by the following equation:

$$V_b = \left( \frac{R_4}{R_3 + R_4} - \frac{R_2}{R_1 + R_2} \right) \cdot V_0$$

where $R_1, R_2, R_3, R_4$ designates the resistance of the first, second, third and fourth arms 102, 112, 122, 132 respectively.

Three different detection loading configurations are contemplated.

In a first configuration referenced as "quarter bridge configuration", the magnetic particles are deposited on a single arm, for instance on the fourth arm 132, the remaining three arms 102, 112, 122 having no magnetic particles thereon.

In this first configuration, the resistances $R_1, R_2, R_3$ of the first, second, third arms 102, 112, 122 equal to a same reference resistance value R, and the resistance $R_4$ of the fourth arm 132 equals to R+ΔR.

In this first case, the detected different voltage denoted $V_{b1}$ follows the equation:

$$V_{b1} = \left( \frac{\Delta R/R}{2(2 + \Delta R/R)} \right) \cdot V_0$$

In a second configuration case referenced as "half bridge configuration", the magnetic particles 12 are deposited onto two opposite arms, for instance onto the second and the third arms 112, 122, the remaining two arms 102, 132 having no magnetic particles thereon.

In this second configuration, the resistances $R_1, R_4$ of the first and fourth arms 102, 132 equal to the same reference resistance value R, and the resistance $R_2, R_3$ of the loaded second and third arms 112, 122 equals to R+ΔR.

In this second configuration the detected different voltage denoted $V_{b2}$ follows the equation:

$$V_{b2} = \left( \frac{\Delta R/R}{2 + \Delta R/R} \right) \cdot V_0$$

In a third configuration referenced as "full bridge configuration", the magnetic particles are deposited onto whole the surface of magnetic sensor, namely the four arms.

In this third configuration, the resistances $R_1, R_4$ of the first and fourth arms 102, 132 equal to the same resistance value R+ΔR, whereas the resistances $R_2, R_3$ of the loaded second and third arms 112, 132 equals to R−ΔR.

In this third configuration the detected different voltage denoted $V_{b3}$ follows the equation:

$$V_{b3} = \frac{\Delta R}{R} \cdot V_0$$

Among the three above described configurations, the full bridge configuration exhibits the highest sensitivity.

Figure 4:
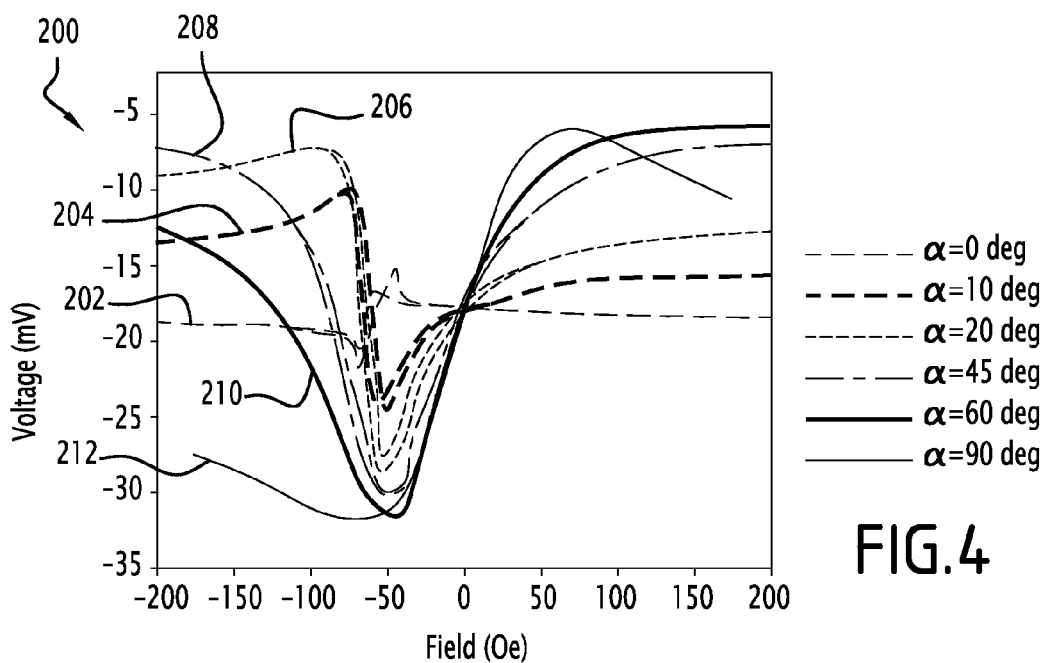
FIG. 4 is a view of different profiles of the detection voltage versus the bias magnetic field, each profile being characterized by the orientation angle α formed between the easy axis of the magnetic sensor and the external magnetic field direction.

According to FIG. 4, the first micro-magnetometry magnetic sensor as described in FIG. 3 is characterized with different values of the bias angle α formed between the easy axis 40 of the magnetic sensor and the magnetic bias field direction.

A set 200 of various profiles 202, 204, 206, 208, 210, 212 are shown corresponding to a bias angle α set to 0, 10, 20, 45, 60, 90 degrees, respectively.

The bias current of the magnetic sensor 4 remains set to 1 mA. The bias magnetic field $H_{DC}$ is swept in the range of −20 to 20 mT.

Figure 5:
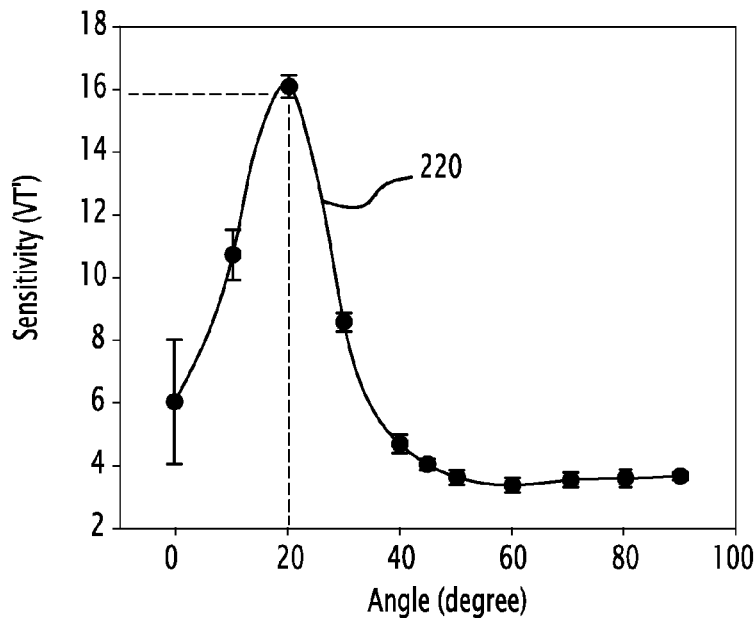
FIG. 5 is a view of the evolution of the sensitivity deduced from the profiles of FIG. 4 versus the orientation angle α.

The sensitivity S at a point of a profile, defined as the slope dV/dH, is deduced from the voltage profiles, the maximum of the sensitivity for each bias angle α value being sketched in the curve 220 as shown in FIG. 5.

The bias angle α formed between the bias magnetic field $H_{DC}$ and the easy axis 40 is selected so that the sensitivity S is maximal.

From the curve 220 shown in the FIG. 5, the sensitivity S is maximal for α equal to 20 degrees and is equal to the 16 V.T$^{-1}$. This value of 20 degrees fir the bias angle α has been chosen in the FIG. 1.

When a micromagnetometry system 2 is used, the effective measured voltage $V_{eff}$ between the two voltage terminals and output from the measurement voltage device contains two contributions: a concave voltage response $V_{drift}$ and a voltage response horizontally caused by the straight field generated from the magnetic particles $V_{stray}$.

Thus, the effective voltage $V_{eff}$ can be expressed as:

$$V_{eff} = V_{drift} + V_{stray}$$

The voltage response of the sensor can be well described by the following expression:

$$V_{drift} = C\frac{I}{t}(\rho_{||} - \rho_{\perp})$$

Where I is the DC bias current applied to the magnetic sensor 4, t, $\rho_{||}$, $\rho_{\perp}$ are, respectively, the thickness and the resistivity of the sensing layer in case of current parallel an perpendicular to magnetization.

Figure 6:
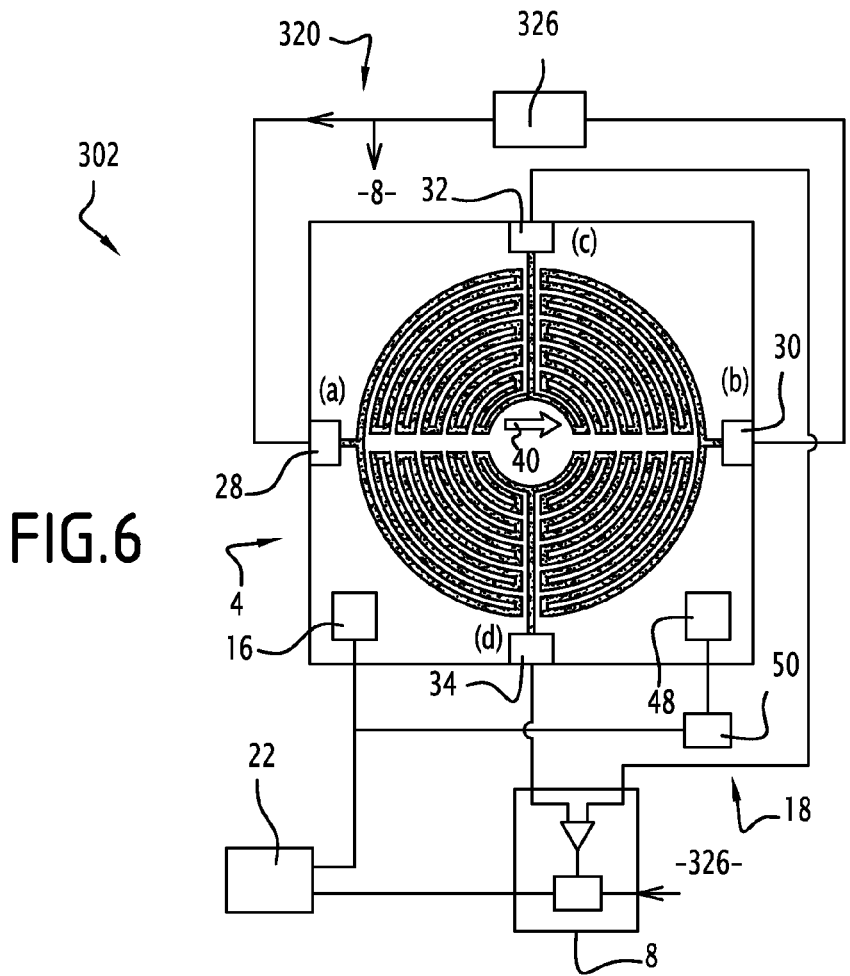
FIG. 6 is a view of the architecture of a micromagnetometry system according to a second embodiment of the invention wherein the exciting magnetic field $H_{AC}$ is generated partly by the first magnetic sensor itself.

According to FIG. 6, a second embodiment of a micromagnetometry system 302 according to the invention is derived from the micromagnetometry system 2 of FIG. 1 and comprises some parts that are designated by the same reference numerals.

The micromagnetometry system 320 of FIG. 6 differs from the micromagnetometry system of FIG. 1 in that the means 20 for creating the magnetic excitation field $H_{AC}$ external to the first magnetic sensor 4 are removed and replaced by the set 320 formed by the first magnetic sensor 4 and a modified first current source 326, connected between the first and second current terminals 28, 30.

In this second embodiment, the modified first current source is configured to generate an alternating current (AC) oscillating along the time at a constant frequency ω ranging from 10 to 3 KHz, here set to 100 Hz.

By self-induction, the magnetic track 24 of the first magnetic sensor 4 supplied with an alternating current (AC) by the first modified current source 326 generates a magnetic excitation field $H_{AC}$ to make produce by each magnetic particle a stray magnetic field, the stray magnetic field being detectable by the first magnetic sensor.

In other words, when the AC bias current I is applied to the first magnetic sensor 4, the magnetic sensor 4 generates a magnetic field globally surrounding the easy axis 40, the direction of the flux obeying the Ampere's law.

The measured voltage Vb between the voltage terminals can be written as:

$$V_b = S_0 \langle H_\perp \rangle + I.R_{offset}$$

Where I is the magnetic sensor current, $S_0$ is the sensivity of the magnetic sensor, $\langle H_\perp \rangle$ is the magnetic field averaged over the surface of the magnetic sensor.

In these measurements, the motionless magnetic particles disposed close to the active surface of the sensor are magnetized by the sensor self magnetic field $H_{self}$.

Using that $H_{self}$ is proportional to I and assuming that the particle magnetization is directly proportional to the applied field, the stray field $\langle H_{stray} \rangle$ from the magnetic particles averaged over the magnetic sensor surface can be written as:

$$\langle H_\perp \rangle = \gamma \chi I$$

where $\chi$ is the susceptibility of the magnetic particle and $\gamma$ is a constant of proportionality depending on the magnetic sensor geometry and on the volume distribution of the magnetic particles.

Using the self field to magnetize the magnetic particles ensures that only the magnetic particles deposited close to the active surface of the first magnetic sensor will be magnetized.

Similarly to the micromagnetometry system of FIG. 1, the measured voltage $V_{eff}$ between the two voltage terminals and output from the measurement voltage device contains two contributions: a concave voltage response $V_{drift}$ and a voltage response horizontally caused by the straight field generated from the magnetic particles $V_{stray}$, and an be expressed as:

$$V_{eff} = V_{drift} + V_{stray}$$

According to FIG. 7, a third embodiment of a micromagnetometry system 402 according to the invention is derived from the micromagnetometry system 2 of FIG. 1 and comprises some parts that are designated by the same reference numerals.

The micromagnetometry system 402 of FIG. 7 differs from the micromagnetometry system of FIG. 1 in that it comprises further a second hybrid AMR/PHR multi-ring magnetic sensor 404 and in that the first voltage measurement device 8 of FIG. 1 is replaced by a modified voltage measurement device 408.

The second magnetic sensor 404 has the same structure as the one of the first magnetic sensor and has closed loop magnetic track 424 with the same shape pattern.

The second magnetic sensor 404 has a first current terminal 428 and a second current terminal 430 forming a pair of current terminals which face each other contacting with the closed loop magnetic track 424.

The second magnetic sensor 404 has a first voltage terminal 432 and a second voltage terminal 434 forming a pair of voltage terminals which face each other contacting with the closed loop magnetic track 424 and from which an output differential voltage is detected.

The second magnetic sensor 404 has an easy axis 440 defined as the axis passing through the first current terminal 428 and the second current terminal 430.

The first and the second magnetic sensors 4, 404 are placed so that their respective easy axis 40, 440 are collinear.

The first and the second magnetic sensors 4, 404 are placed close to each other on the same substrate under the same known physical conditions so that the same magnetic field when no magnetic particles are deposited onto the sensors with the same noise are received and detected.

The first current terminal 428 and the second current terminal 430 of the second magnetic sensor are respectively connected to the first current terminal 28 and the second current terminal 30 of the first magnetic sensor 4.

Thus, the first current or voltage source 6 supplies with in parallel the first magnetic sensor 4 and the second magnetic sensor 404 with respective current having the same noise characteristics.

The modified first voltage measurement device 408 is based upon the first voltage measurement device 8 of FIG. 1, wherein a second low noise amplifier 444 and a differential unit 450.

The second low noise amplifier 444 with a gain of 20 dB is connected at its inputs to a first voltage terminal 432 and a second voltage terminal 434 and at its output to a first input of the differential unit 450.

The first low noise amplifier 4 is connected at its output to a second input of the differential unit 450.

The differential unit 450 has an output connected to the synchronizing amplifying device 46 based on a phase lock loop.

The differential unit 450 is configured to determine the difference voltage between the amplified differential voltage detected at the voltage terminals of the first magnetic sensor 4 and the amplified differential voltage detected at the voltage terminals of the second magnetic sensor 404.

Thus the sources of noises common to the two magnetic sensors are canceled by the subtraction unit 450.

As a variant of the micromagnetometry system 402 of FIG. 7, the means 20 for creating the magnetic excitation field $H_{AC}$ external to the first magnetic sensor 4 are removed and replaced by the set 320 formed by the first magnetic sensor 4 and a modified first current source 326, connected between the first and second current terminals 28, 30.

According to FIG. 8, a first embodiment of a micromagnetometry detection method 500 for detecting the presence of very small quantities of magnetic particles is carried out by a micromagnetometry system as defined in the FIGS. 1, 6 and 7.

This method 500 is applicable to any for magnetic particles that are switchable molecular nanoparticles by overstepping a predetermined switching threshold in terms of a switching physical property that operates as a switching command. Such magnetic particles are any switchable molecular nanoparticles in form of $A_h B_k[M(CN)_6]_l \cdot mH_2O$, where A can be Co, Ni, Fe, etc, B and M can be various transition metals ($Fe^{II}$, $Fe^{III}$, $Mn^{II}$ $Mn^{III}$, fml $aCo^{II}$, $Co^{III}$, ...) and C is an alkali metal.

The micromagnetometry detection method 500 comprises the following steps executed successively.

In a first step 502, an unknown amount of magnetic particles is deposited upon the first magnetic sensor, the magnetic particles being switchable molecular nanoparticles by overstepping a predetermined switching threshold in terms of a switching physical property that operates as a switching command.

In a following step 504, under known predetermined physical conditions, by varying the physical property magnitude over a predetermined range of the physical property, when the magnetometry system comprises a first single magnetic sensor, a first curve as the evolution of differential voltage measurements carried out by the first sensor versus the magnitude of the physical property is provided, or when the magnetometry system comprises a first magnetic sensor and a second magnetic sensor, a first set of differential voltage measurements carried out by the first sensor that has magnetic particles thereon and a second set of differential voltage measurements carried out by the second sensor that has no magnetic particles thereon are outputted, and a first curve is determined as the evolution versus the physical property of the difference between the first set of differential voltage measurements and the second set of differential voltage measurements.

Then, in a following step 506, over the predetermined range of the physical property a second curve is determined as a fitting curve from a lower portion of the first curve, this lower portion of the first curve corresponding to a lower interval included within the predetermined range of the physical property having its upper bound lower than the predetermined switching threshold.

Then, in a step 508, a third curve is determined as the difference versus the magnitude of the switching physical property between the differential voltages of the first curve and the differential voltages of the second curve within the same range of magnitude of the physical property.

In a next step 510, the presence of magnetic particles is detected when the third curve the third curve exhibits a switching physical property interval over which a transition occurs and when the amplitude of the transition is greater than the predetermined detection threshold, the predetermined detection threshold corresponding to a minimal magnetization field shift detectable of 10 nT.

Figure 9:
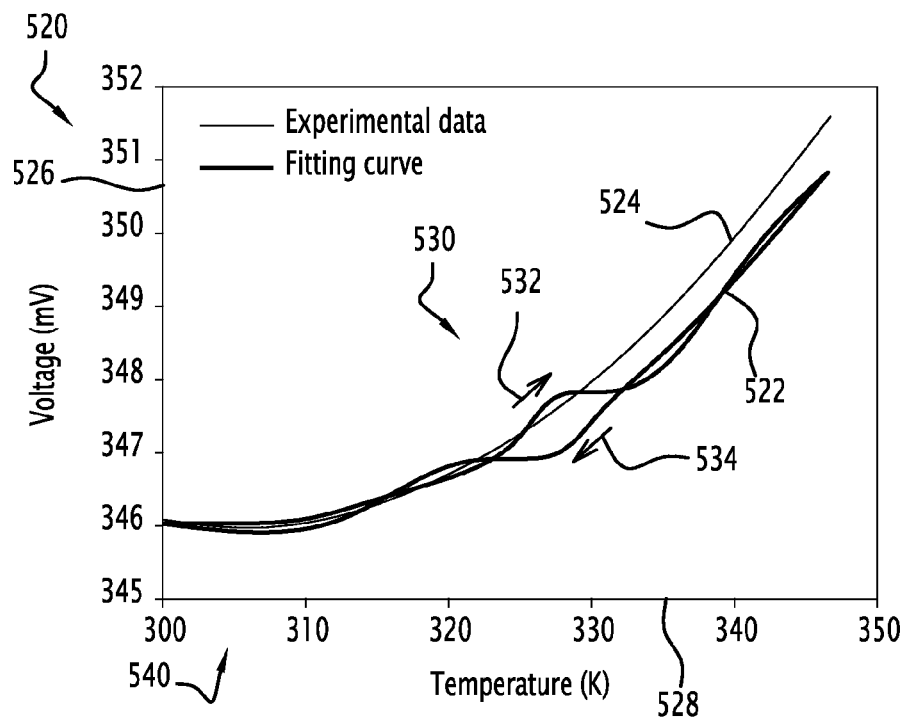
FIG. 9 is an exemplary view of a first curve of the evolution versus temperature of measurement voltages provided by the micromagnetometry system of FIG. 1 when SCO particles are deposited on the active surface of the first magnetic sensor the temperature ranging from 300 K to 350 K, and of a corresponding fitting second curve determined by the method of FIG. 6.

According to FIG. 9, a representative voltage profile 522 evolution of the effective voltage $V_{eff}$ outputted by the micromagnetometry system 2 versus the environmental temperature T, and a fitting curve 524 are shown in a representation frame 520.

The representation frame 520 comprises an ordinate axis 526 of the outputted voltage expressed in mV and an abscissa axis 538 of the environmental temperature axis expressed in degree Kelvin.

The voltage profile 522 exhibits two contributions: a concave voltage response $V_{drift}$ and a voltage response horizontally caused by the straight field generated from the SCO particles $V_{stray}$.

Thus, the effective voltage $V_{eff}$ can be expressed as:

$$V_{eff} = V_{drift} + V_{stray}$$

The voltage profile 522 also exhibits a hysterisis loop 530 having an upper curve portion in heating direction 532 and an lower curve portion in cooling direction 534. This hysterisis loop 530 is a magnetic signature of the SCO particles transition.

In practice, the voltage response of the magnetic sensor $V_{drift}$ curve 524 is determined over the range of temperature [300 K, 350 K] as a fitting curve from a lower portion of voltage profile 522, this lower portion of the voltage profile 522 corresponding to a lower temperature interval included within the predetermined range of the physical property having its upper bound lower than the predetermined switching threshold. For example, the lower temperature interval is [300 K, 320 K].

Figure 10:
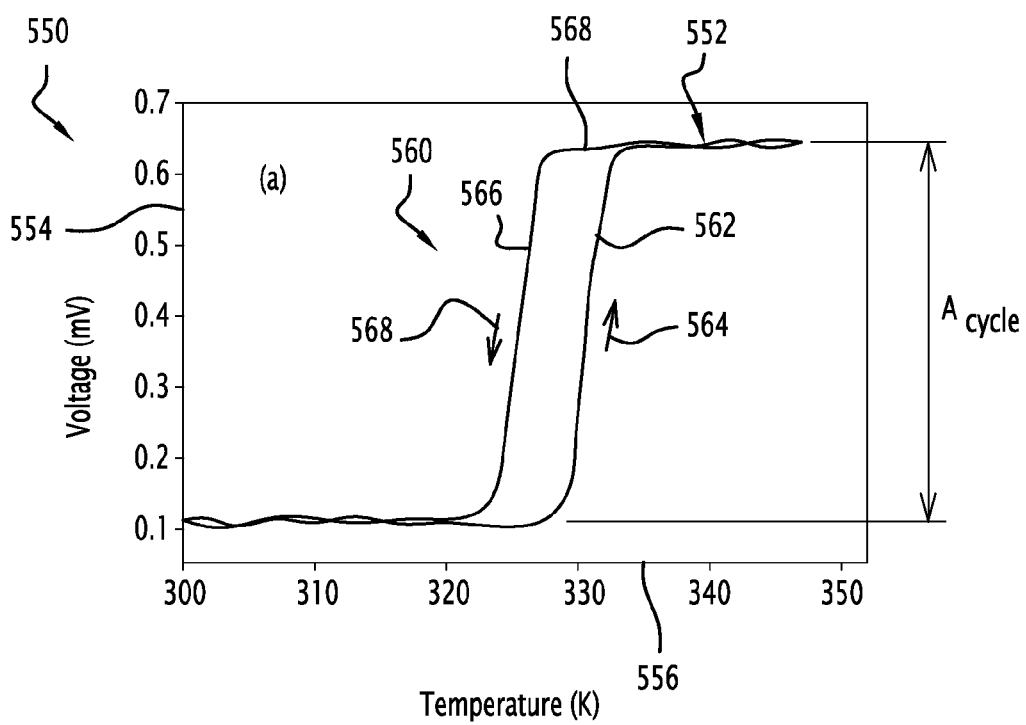
FIG. 10 is a view of the third curve determined from the first and second curves of FIG. 7 according to the method of FIG. 6.

According to FIG. 10, a voltage profile 552 evolution of the stray field voltage $V_{stray}$ versus the environmental temperature T is shown in a representation frame 550.

The voltage profile 552 evolution of the stray field voltage $V_{stray}$ is derived from the subtraction of the voltage drift $V_{drift}$ curve 524 to the effective voltage $V_{eff}$ 522.

The subtraction is carried out by the processing unit 22 in the step 508 of the detection method 500.

The representation frame 550 comprises an ordinate axis 554 of the stray field voltage $V_{stray}$ expressed in mV and an abscissa axis 556 of the environmental temperature axis expressed in degree Kelvin.

The voltage profile 552 exhibits a hysterisis loop 560 having a lower curve portion 562 in heating direction 564 and an upper curve portion 566 in cooling direction 568.

This hysterisis loop 560 is a magnetic signature of the SCO particles transition.

The transition temperatures are picked up at the middle eight of the hysteresis curves of the hysteresis loop 560.

With the dimensioning and the performance of the first magnetic sensor 4 as described here above, and with an average diameter of 250 nm for the SCO particles, the minimum magnetic field that can be detected by the magnetic sensor is equal to 10 nT.

As the detection capability of the magnetometer 2 depends on the sensor area, it is expected that by sizing the magnetic sensor to 500 nm, a single magnetic particle will deduce an amount of 25 nV. This makes possible to detect the magnetic signature of a single SCO particle at room temperature.

By integrating an amplifier in the close vicinity of the magnetic sensor or near the two magnetic sensors in the differential configuration, a local magnetic field down to one pico-Tesla ($10^{-12}$ T) can be detected.

Generally, the width of one arm of the sensor ring is ranging from the nano-scale to the micro-scale and the effective size of the magnetometry is ranging from 50 nm to 1 mm.

Figure 11:
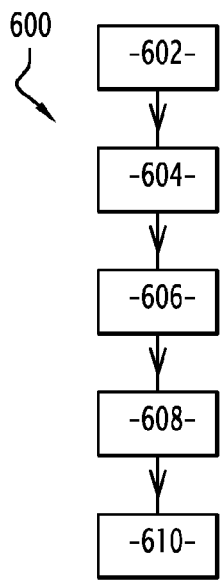
FIG. 11 is an example of flow diagram of a micromagnetometry detection method according a second embodiment of the invention carried out for a broader family of magnetic particles including magnetization switchable molecular nanoparticles, paramagnetic particles, ferromagnetic particles, anti-ferromagnetic particles, magnetic beads made of $Fe_3O_4$ in a polymer matrix.

According to FIG. 11, a second embodiment of a micromagnetometry detection 600 method is carried out for detecting the presence of very small quantities of magnetic particles.

This method 600 is applicable to any for magnetic particles that are switchable molecular nanoparticles by overstepping a predetermined switching threshold in terms of a switching physical property that operates as a switching command. Such magnetic particles are any switchable molecular nanoparticles in form of $A_hB_k[M(CN)_6]_l \cdot mH_2O$, where A can be Co, Ni, Fe, etc, B and M can be various transition metals ($Fe^{II}$, $Fe^{III}$, $Mn^{II}$, $Mn^{III}$, fml a$Co^{II}$, $Co^{III}$ ...) and C is an alkali metal cation.

This method is also applicable to any paramagnetic particles such as $Fe_2O_3$, $Fe_3O_4$, Fe@$Fe_3O_4$, CoFe@$Fe_3O_4$, Ni, to any ferromagnetic particles such as Fe, CoFe, Ni, to any antiferromagnetic particles i.e any particles with multilayer structure Ti/Fe, Cr, NiO, $Co_3O_4$, a-$Fe_2O_3$, CuO, MnO, $Cr_2O_3$ nanoparticles, and to any magnetic bead made of $Fe_3O_4$ in the polymer matrix with the sphere shape and any size ranging from 50 nm to 10 µm.

The micromagnetometry detection method 600 for detecting the presence of very small quantities of magnetic particles can be carried out by a micromagnetometry system as defined in the FIGS. 1, 6 and 7.

The micromagnetometry detection method 600 comprises the following steps executed successively.

In a first step 602, under first known predetermined physical conditions, when the system comprises a single first magnetic sensor 4 the first magnetic sensor is, or when the magnetometry system comprises a first magnetic sensor 4 and a second magnetic sensor 404 the set of the first and second magnetic sensor is calibrated in temperature and a first calibration background thermal noise curve is provided.

In a following step 604, an unknown amount of magnetic particles 12 is deposited upon the first magnetic sensor 4.

Then in a next step 606, under the same first known predetermined physical conditions, by varying temperature on a predetermined range of temperature, when the magnetometry system 2, 302 comprises a first single magnetic sensor 4, a second curve is outputted as the evolution of differential voltage measurements carried out by the first sensor versus temperature, or when the magnetometry system 402 comprises a first magnetic sensor 4 and a second magnetic sensor 404, a first set of differential voltage measurements carried out by the first sensor 4 that has magnetic particles thereon and a second set of differential voltage measurements carried out by the second sensor 404 that has no magnetic particles thereon are outputted. In the same step 506 a second curve is determined as the evolution versus temperature of the difference between the first set of differential voltage measurements and the second set of differential voltage measurements.

In a following step 608, a third curve is determined as the difference versus temperature between the differential voltages of the second curve and the differential voltages of the first curve within the same range of temperature.

Then, in a next step 610, the presence of magnetic particles is detected when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

Figure 12:
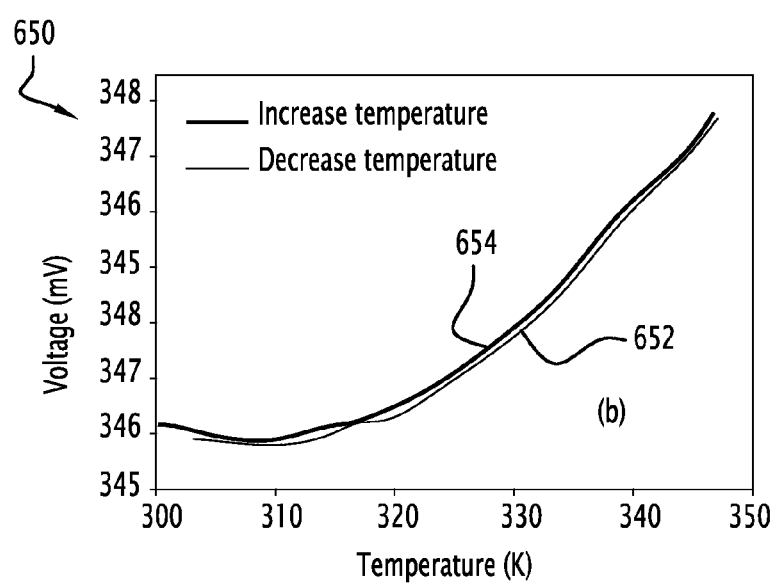
FIG. 12 is a view of a calibration background noise curve representative of the thermal magnetic response of the first magnetic sensor without any magnetic particles deposited thereon.

According to FIG. 12, an example of a first calibration background thermal noise 650 profile is shown.

This calibration of the first magnetic sensor 4 or the set of the first and second magnetic sensor 4, 44 is carried out in the step 602 of the detection method 600.

During this thermal calibration step the first magnetic sensor 4 is unloaded i.e. without any magnetic particles deposited thereon and temperature is varied in the temperature once by increasing the temperature and once by decreasing the temperature.

The profile 650 comprises a first curve 652 corresponding to a heating direction and a second curve 654 corresponding to a cooling direction. These curves are identical and the calibration profile 650 does not exhibit any hysterisis cycle.

Figure 13:
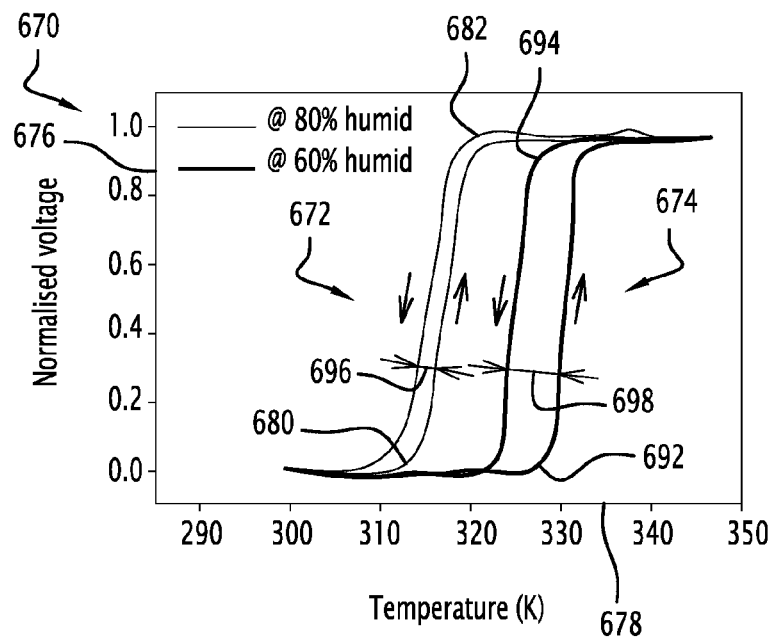
FIG. 13 is a view of transition temperatures of SCO particles detected under two different humidity conditions, 80% and 60% respectively.

According to FIG. 13, a set of two different hysterisis cycles or loops 672, 674 with their corresponding transition temperatures are shown for same used SCO particles detected under two different humidity conditions, 80% and 60% respectively.

These two hysterisis cycles 672, 674 are shown in a representation frame 670 that comprises an ordinate axis 676 of the normalized output voltage to an upper voltage and lower voltage of the hysterisis cycle and an abscissa axis 678 of the environmental temperature axis expressed in Kelvin degree.

The hysterisis loop 672 corresponding to 80% humidity exhibits a first transition temperature 680 and a second transition temperature 682.

The hysterisis loop 674 corresponding to 60% humidity exhibits a first transition temperature 692 and a second transition temperature 694.

It can be seen here that the transition temperatures as well as the width of a hysterisis loop can be used to estimate the humidity degree.

Such behaviour is therefore exploited to build a humidity measurement system comprising a micromagnetometry system as described in FIGS. 1, 6, and 7 wherein the particles are molecular nanoparticles switchable by overstepping a predetermined temperature switching threshold and sensitive to humidity degree, the predetermined temperature switching threshold or an hysteris loop width depending on the humidity degree environment.

The processing unit is configured to determine the humidity degree from magnetic change measurements of the magnetic particles and a previously determined mapping curve between calibrated humidity degrees measured by another humidity measurement method and a corresponding temperature transition or hysterisis cycle width measured by the micromagnetometry method as described in FIG. 8 or FIG. 11.

In fact, by combining the magnetometry method of FIG. 8 or FIG. 11 and spin crossover, the system can be used as a gas sensor for detecting gas. Any external gas that affects the system like the humidity also shifts the spin crossover curves as a function of the environment gas concentration.

Thus any molecular nano-particles which are switchable by overstepping a predetermined temperature switching threshold, the predetermined temperature switching threshold depending on the environment concentration of some vapour of external molecules, can be used.

In such case, the processing unit is configured to determine the environment concentration of the vapour of external molecules from magnetic change measurements of magnetic particles that are sensitive to the environment concentration of the vapour of external molecules, and from a previously determined mapping curve between a calibrated environment concentration of the vapour of external molecules measured by another method and a corresponding parameter such as a temperature threshold, a transition temperature, or a width of an hysterisis loop determined through the magnetic property change of the magnetic particles detected by the micromagnetometry method described in FIG. 8 or FIG. 11.

The vapour of external molecules or the gas that can be detected are for example the following ones:

$N_2$, He, $I_2$, $CO_2$, ethanol, methanol, 2-propanol, acetone, $D_2O$, $CS_2$, CO, Iode (I), brome (Br), chlore (Cl), benzene, toluene, chlorobenzene, bromobenzene, iodobenzene, dichlorobenzene, trichlorobenzene, pyrazine, pyridine, pyrrole, thiophene, furane, thf.

The detection method 600 as described above in FIG. 11 can be used for detection of the following particles:

Any switchable molecular nanoparticles in form of $A_hB_k[M(CN)_6]_l.mH_2O$, where A can be Co, Ni, Fe, etc, B and M can be various transition metals ($Fe^{II}$, $Fe^{III}$, $Mn^{II}$, $Mn^{III}$, $Co^{II}$, $Co^{III}$, ...) and C is an alkali metal cation;

Any paramagnetic particles: $Fe_2O_3$, $Fe_3O_4$, $Fe@Fe_3O_4$, $CoFe@Fe_3O_4$, Ni, ...;

Any ferromagnetic particles: Fe, CoFe, Ni;

Any antiferromagnetic particles: any particles with multilayer structure Ti/Fe, Cr, NiO, $Co_3O_4$, a-$Fe_2O_3$, CuO, MnO, $Cr_2O_3$ nanoparticles:

Any magnetic bead made of $Fe_3O_4$ in the polymer matrix with the sphere shape and any size ranging from 50 nm to 10 µm.

This system can be used to detect a magnetization variation (magnetization commutation) of all magnetic materials (paramagnetic, diamagnetic, ferromagnetic, antiferromagnetic, ferrimagnetic) in different forms (materials in the form of microcrystalline powders, nanoparticles, thin layer, etc.) and at any temperature. As representative examples, the following can be cited: metallic materials, metallic oxides, rare earth elements, organometallic complexes, coordination complexes (magnetic molecules, magnet chains, and in particular spin cross-over materials, transfer of load materials, etc.

Metals, Metal Oxides

As representative metal derivatives, the following can be cited: compounds such as Co, Ni, Fe, etc., as well as alloys AB, with A=Co, Ni, Fe, etc. and B=Pt, Fe, etc.

As representative metal oxides derivatives, the following can be cited: FeO, $Fe_2O_3$, CuO, ZnO, etc.

Magnetic Compounds and Molecular Complexes

As representative magnetic compounds and molecular complexes can be cited magnet molecules (Mn12, etc.), magnet chains (homopolynuclear and heteropolynuclear compounds), etc.

As heteropolynuclear magnetic compounds, one can cite Prussian Blue and its analogues of general formula $M_x[M'(CN)_6]_y.nH_2O$ et $A_xM_y[M'(CN)_6].nH_2O$ where A represents an alkaline cation and M and M' represent cations of divalent or trivalent transition metals such as $Fe_4[Fe(CN)_6]_3.15H_2O$, $CsNi[Cr(CN)_6]$, etc.

As spin cross-over materials can be cited iron complexes, in particular of formula (I):

$$Fe[(L)3](X)2.xH2O \qquad (I)$$

in which:
 L represents a ligand such as trz (triazole), $NH_2$trz, Fatrz ((4-formylamino-1,2,4-triazol), Hptrz (heptyltriazole), etc.;
 X represents an anionic counterion such as OTf (triflate ou trifluoromethanesulfonate), p-tol or tof (p-tolylsulfonate or tosyl), tetrafluoroborate, nitrate, Br, Cl, etc.;
 x is an integer comprised between 0 et 10.

As alternative spin cross-over materials, one can cite the derivatives of general formula (II):

where:
 M represents a metal such as Ni or Co;
 M' represents a metal, identical or different from M, chosen from Ni, Pd, Pt, etc;
 L represents a bis-monodente ligand such as pyrazine (pz), azopyridine (azpy), bis(4-pyridyl)acetylene (bpac), etc.;
 y is strictly comprised between 0 and 1, being different from 0 and from 1.

As a load transfer compounds, one can cite the derivatives formed by donor/acceptor pairs such as compound of formula [Fe(Cp*)$_2$][TCNE] (TCNE=tetracyanoethylene), [Mn(Cp*)$_2$][TCNQ] (TCNQ=tetracyanoquinodimethane), etc.

Other load transfer materials according to the invention also include the analogues of Prussian Blue of general formula $A_xM_y[M'(CN)_6].nH_2O$ with A being a alkaline cation and M and M' representing cations of divalent or trivalent transition metals such as $Na_xCo_y[Fe(CN)_6].nH_2O$, etc.

The detection method 500 as described above in FIG. 8 can be used for detection of any switchable molecular nanoparticles as described above.

In a variant the current injected by the first current source passing through the current terminals is a sum of a direct current (DC) and an alternating current (AC).

Generally, the magnetic track is a bi-layered structure including a ferromagnetic film and an anti-ferromagnetic film, or a spin-valve structure, or a tri-layered structure including a ferromagnetic film, a metal and an anti-ferromagnetic film.

In a variant of the micromagnetometry system 402 of FIG. 7, the first and second hybrid AMR/PHR multi-ring magnetic sensors 4, 404 are replaced by magnetic sensors having a same magnetic structure and a same shape amongst a cross shape or a single ring closed loop shape.

The first and the second magnetic sensors with a same shape amongst a cross shape or a single ring closed loop shape are placed so that their respective easy axis, are collinear in terms of direction i.e are parallel between each other.

The first and the second magnetic sensors are placed as close as possible on the same substrate under the same known physical conditions so that the same magnetic and temperature response when no magnetic particles are deposited onto the sensors with the same noise are received and detected.

The first current terminal and the second current terminal of the second magnetic sensor are respectively connected to the first current terminal and the second current terminal of the first magnetic sensor.

Thus, the first source current supplies with in parallel the first magnetic sensor and the second magnetic sensor with respective current having the same noise characteristics.

The structure of the modified voltage measurement device 408 remains the same and the modified voltage measurement device is configured to determine the difference voltage between the amplified differential voltage detected at the voltage terminals of the first magnetic sensor and the amplified differential voltage detected at the voltage terminals of the second magnetic sensor.

Thus the sources of noises common to the two magnetic sensors are canceled.

As for the micromagnetometry system 402 of FIG. 7, the means 20 for creating the magnetic excitation field $H_{AC}$ external to the first magnetic sensor 4 can be removed and replaced by a set formed by the first magnetic sensor, the second magnetic sensor and a modified first current source generating an alternating current between the first and second current terminals of the first magnetic sensor, and between the first and second current terminals of the second magnetic sensor.

In fact all the variants described for a magnetometry system using one or two multi-ring magnetic sensors as described here above in terms of current biasing and means for creating an external magnetic field can be used for a magnetometry system using two magnetic sensors having a same shape amongst a cross shape or a single ring closed loop shape, and connected between each other in a differential way.

The same detection methods as described in FIGS. 5 and 8 can also be used.

Figure 14:
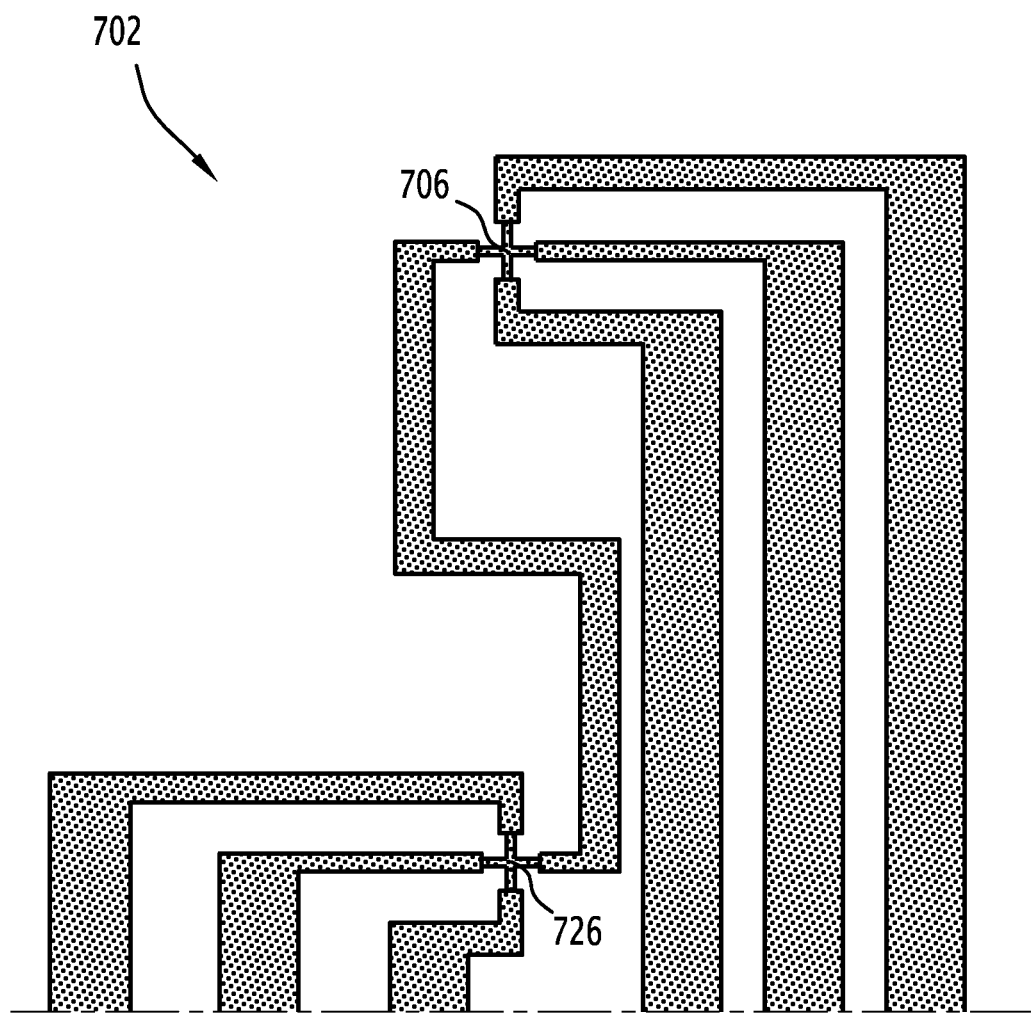
FIG. 14 is a partial view of an example of a variant of the micromagnetometry system of FIG. 7 wherein the two multi-ring magnetic sensors are replaced by cross shape magnetic sensors.

An example of such a variant of micromagnetometry system 702 is partly illustrated in FIG. 14 wherein the two multi-ring magnetic sensors 4, 404 of FIG. 7 are replaced by two cross shape magnetic sensors 706, 726.

The first and the second magnetic sensors 706, 726 with the same cross shape are placed close to each other on the same substrate under the same known physical conditions so that the same magnetic field when no magnetic particles are deposited onto the sensors with the same noise are received and detected.

The first and the second magnetic sensors 706, 726 are placed so that their respective easy axis are collinear in terms of direction i.e are parallel between each other.

In a variant, when the micromagnetometry system used comprises a first and a second hybrid AMR/PHR multi-ring magnetic sensors 4, 404 as described in FIG. 7 or comprises two magnetic sensors having a same magnetic structure and a same shape amongst a cross shape or a single ring closed loop shape, a direct detection method can be used.

Such a micromagnetometry direct detection method is used for detecting the presence of very small quantities of magnetic particles down to a single magnetic particle or a single magnetic object in nano or micro scale.

A micromagnetometry direct detection method according to a first embodiment comprises the following steps.

After depositing an unknown amount of magnetic particles or a magnetic object upon the first magnetic sensor, in a first step, under known predetermined physical conditions, a first voltage measurement carried out by the first sensor that has magnetic particles thereon and a second voltage measurement carried out by the second sensor that has no magnetic particles thereon are outputted.

In a second step, a first difference between the first voltage measurement and the second voltage measurement is determined.

In a third step, the presence of magnetic particles or a magnetic object is detected when a second difference as the difference between the first difference and a reference difference has an amplitude greater than a predetermined detection threshold, the reference difference being the difference between a first voltage measurement carried out by the first sensor that has no magnetic particles thereon and a second voltage measurement carried out by the second sensor that has no magnetic particles thereon under the same known predetermined physical conditions, and the predetermined detection threshold corresponding to a minimal magnetization field shift detectable of 10 nT.

A micromagnetometry direct detection method according a second embodiment is applicable when the magnetic particles are molecular nanoparticles or a single object switchable by overstepping a predetermined switching threshold in terms of a switching physical property that operates as a switching command.

The direct detection method comprises the following steps.

After depositing an unknown amount of magnetic particles or a magnetic object upon the first magnetic sensor, in a first step, under known predetermined physical conditions, the physical property magnitude is varied over a predetermined range of the physical property.

In a second step carried in parallel with the first step, a first set of voltage measurements carried out by the first sensor (4) that has magnetic particles thereon and a second set of voltage measurements carried out by the second sensor (404) that has no magnetic particles thereon are outputted.

In a third step, a curve is determined as the evolution versus the physical property magnitude of the difference between the first set of differential voltage measurements and the second set of voltage measurements.

In a fourth step, the presence of magnetic particles or magnetic object is detected when the curve exhibits a switching physical property interval over which a transition occurs having an amplitude greater than the predetermined detection threshold, the predetermined detection threshold corresponding to a minimal magnetization field shift detectable of 10 nT.

The invention claimed is:

1. Micromagnetometry system for detecting the presence of very small quantities of magnetic particles down to a single magnetic particle or a single magnetic object in nano or micro scale comprising:

a first magnetic hybrid Anisotropic Magneto-Resistive (AMR)/Planar Hall Resistive (PHR) multi-ring sensor having an active surface including a magnetic track of a closed loop shape deposited on a substrate, a first current terminal and a second current terminal forming a pair of current terminals which face each other contacting with the closed loop magnetic track made of a magnetic material, a first voltage terminal and a second voltage terminal forming a pair of voltage terminals which face each other contacting with the closed loop magnetic track and from which an output differential voltage $V_b$ is detected, a first axis passing through the first and second current terminals being parallel to the exchange bias field direction of the track material and perpendicular to a second axis passing through the first and second voltage terminals;

a first current or voltage source connected between the first and second current terminals for injecting a current I therethrough;

a first voltage measurement device connected between the first and second voltage terminals for measuring the differential voltage $V_b$ between the pair of voltage terminals;

a set of at least one magnetic particles deposited on the active surface of the first magnetic sensor;

a processing unit for detecting from a set of different measured differential voltages a magnetic flux shift representative of the presence of a least one deposited magnetic particle;

the magnetic track of the first AMR/PHR multiring magnetic sensor having:

a first arm made of a first set of a predetermined ring number m lower than 18 of circular meander paths delimited within a first quarter surface of the first magnetic sensor, the outermost meander path being connected to the first current terminal and the innermost meander path being connected to the first voltage terminal, a second arm made of a second set of the same predetermined number m of circular meander paths delimited within a second quarter surface of the first magnetic sensor, the outermost meander path being connected to the second current terminal and the innermost meander path being connected to the first voltage terminal, a third arm made of a third set of the same ring number m of circular meander paths delimited within a third quarter surface of the first magnetic sensor, the outermost meander path being connected to the second current terminal and the innermost meander path being connected to the second voltage terminal, a fourth arm made of a fourth set of the same ring number m of circular meander paths delimited within a fourth quarter surface of the first magnetic sensor, the outermost meander path being connected to the first current terminal and the innermost meander path being connected to the second voltage terminal;

the magnetic track is a bi-layered structure including a ferromagnetic film and an anti-ferromagnetic films, or a spin-valve structure, or a tri-layered structure including a ferromagnetic film, a metal and an anti-ferromagnetic film;

wherein the micro-magnetometry system comprises a magnetic field generator configured to create a magnetic excitation field $H_{AC}$ to make each magnetic particle produce a stray magnetic field, the magnetic excitation field $H_{AC}$ oscillating along the time at a constant frequency $\omega$ ranging from 10 to 3 KHz; and the magnetic particles to be detected are motionless and placed close to or in contact with the active surface of the magnetic track (24); and the current I injected by the first current or voltage source passing through the current terminals is a direct current (DC), or an alternating current (AC), or a sum of a direct and an alternating current; and the processing unit is configured to either provide with a first calibration curve of a background thermal magnetic response of the first magnetic sensor without any magnetic particles deposited thereon, over a predetermined temperature range, under first known predetermined environmental physical conditions, and under a first set of known system operating conditions in terms of the injected current by the first current or voltage source and of the magnetic excitation field $H_{AC}$ applied; then after deposit of an unknown amount of magnetic particles upon the first magnetic sensor, determining a second curve of the evolution versus temperature of differential voltage measurements corrected or not from a set of differential voltage measurements output from the first magnetic sensor and carried out by varying the temperature over the same predetermined range of temperature, under the same first known predetermined environmental physical conditions and under the same first set of known system operating conditions, then to determine a third curve as the difference the second curve and the first curve over the same range of temperature; and to detect the presence of at least one magnetic particle when the absolute value of all the voltage differences of the third curve remains above a predetermined detection threshold or when the third curve exhibits a temperature interval over which a transition occurs having an amplitude greater than the predetermined detection threshold, the predetermined detection threshold corresponding to a minimal magnetization field shift detectable of 10 nT; or, after deposit of an unknown amount of magnetic particles upon the first magnetic sensor, the magnetic particles being switchable molecular nanoparticles by overstepping a predetermined switching threshold in terms of a switching physical property that operates as a switching command, by varying the physical property magnitude over a predetermined range of the physical property under known predetermined physical conditions and under known system operating conditions, to determine a first curve of the evolution of differential voltage measurements corrected or not from the evolution of differential voltage measurements carried out by the first magnetic sensor versus the magnitude of the physical property; then to determine over the predetermined range of the physical property magnitude a second curve as a fitting curve from a lower portion of the first curve, this lower portion of the first curve corresponding to a lower interval included within the predetermined range of the physical property, the lower interval having its upper bound lower than the predetermined switching threshold; then to determine a third curve as the difference versus the magnitude of the switching physical property between the differential voltages of the first curve and the differential voltages of the second curve within the same range of magnitude of the physical property; and to detect the presence of magnetic particles when the third curve exhibits a switching physical property interval over which a transition occurs having an amplitude greater than the predetermined detection threshold, the predetermined detection threshold corresponding to a minimal magnetization field shift detectable of 10 nT.

2. Micromagnetometry system according to claim 1, comprising further a first environmental temperature sensor for measuring an environmental temperature and/or a second environmental sensor for measuring a physical property different from the environmental temperature placed close to the active surface of the first active sensor, the switching of a magnetization of the magnetic particles being actuated when temperature or the physical property different of temperature is above or below a predetermined switching threshold.

3. Micromagnetometry system according to claim 2, comprising further a controller/regulator configured to control and/or regulate the environmental temperature and/or the physical environmental property different from the temperature.

4. Micromagnetometry system according to claim 1, wherein the magnetic field generator comprises a second current source supplying an AC current and a least one coil connected to the second AC current source, the at least one coil being positioned relative to the first magnetic sensor so that the magnetic excitation field $H_{AC}$ has a main component collinear to the first axis.

5. Micromagnetometry system according to claim 4, comprising further a magnetic sensor bias field generator configured to create a magnetic sensor bias field $H_{DC}$ to shift the operating point of the first magnetic sensor to a highest sensing region, the magnetic sensor bias field $H_{DC}$ being constant along the time, and being collinear with the magnetic excitation field $H_{AC}$ created by the magnetic field generator.

6. Micromagnetometry system according to claim 5, wherein the angle $\alpha$ formed between the first axis passing through the first and second current terminals and the axis of magnetic sensor bias field $H_{DC}$ is in the range from 0 degree to 90 degrees so that the sensitivity of the magnetic sensor is maximal.

7. Micromagnetometry system according to claim 1, wherein the magnetic field generator is the current or voltage source connected between the first and second current terminals, the current or voltage source being configured to generate an alternating current (AC) oscillating along the with time at a constant frequency $\omega$ ranging from 10 Hz to 3 KHz.

8. Micromagnetometry system according to claim 1, comprising further a second magnetic hybrid AMR/PHR multi-ring sensor having the same structure as the first magnetic hybrid AMR/PHR multi-ring sensor, the first and the second magnetic hybrid AMR/PHR multi-ring sensors being placed close to each other on the same substrate under the same known physical conditions to measure the same magnetic field when no magnetic particles are deposited onto the sensors, the second magnetic hybrid AMR/PHR multi-ring sensors having a first current terminal and a second current terminal forming a pair of current terminals connected in parallel to and sharing the same first current source of the first magnetic hybrid AMR/PHR multiring sensor; and wherein the micromagnetometry system is configured to differentiate a first set of differential voltage measurements carried out by the first sensor corresponding to a first configuration wherein magnetic particles to be detected if they are contained in the solution dropped are deposited on the first magnetic sensor and placed under a set of known environmental conditions and system operating settings, and a second set of reference differential voltage measurements carried out by the second sensor corresponding to a second configuration wherein no magnetic particles are deposited thereon, under the same set of known environmental physical conditions and system operating settings and to provide a corresponding difference curve; and then to detect from the difference curve an abrupt variation corresponding at least to a minimal magnetization field shift of 10 nT.

9. Micromagnetometry system for detecting the presence of very small quantities of magnetic particles down to a single magnetic particle or a single magnetic object in nano or micro scale comprising:

a first magnetic hybrid AMR/PHR sensor and a second magnetic hybrid AMR/PHR multiring sensor, the first magnetic hybrid AMR/PHR sensor having a first active surface comprising a first magnetic track deposited on a substrate, a first current terminal and a second current terminal forming a pair of current terminals which face each other contacting with the first magnetic track made of a magnetic material, a first voltage terminal and a second voltage terminal forming a pair of voltage terminals which face each other contacting with the first magnetic track and from which an output differential voltage is detected, a first axis passing through the first and second current terminals being parallel to the exchange bias field direction of the track material and perpendicular to a second axis passing through the first and second voltage terminals;

wherein the micromagnetometry system comprises a second magnetic hybrid AMR/PHR sensor being placed close to the second magnetic hybrid AMR/PHR sensor on the same substrate under the same known physical conditions to measure the same magnetic field when no magnetic particles are deposited onto the sensors, the second magnetic hybrid AMR/PHR multi-ring sensor having a second active surface including a second magnetic track deposited on the same substrate, a first current terminal and a second current terminal forming a pair of current terminals which face each other contacting with the second magnetic track made of a magnetic material, a first voltage terminal and a second voltage terminal forming a pair of voltage terminals which face each other contacting with the second magnetic track and from which an output differential voltage is detected, a first axis passing through the first and second current terminals being parallel to the exchange bias field direction of the track material and perpendicular to a second axis passing through the first and second voltage terminals, the first and the second magnetic tracks having a same shape amongst a cross shape, a single ring closed loop shape and a multi-ring closed loop shape, and having a same layer structure, the layer structure of the first and the second magnetic tracks being a bi-layered structure including a ferromagnetic film and an anti-ferromagnetic films, or a spin-valve structure, or a tri-layered structure including a ferromagnetic film, a metal and an anti-ferromagnetic film;

and in that the micro-magnetometry system comprises:

a same first current or voltage source connected to and supplying in parallel a current I to the first magnetic hybrid AMR/PHR sensor and the second magnetic hybrid AMR/PHR multi-ring sensor, a first voltage measurement device connected at its input to the first and second voltage terminals of the first magnetic hybrid AMR/PHR sensor and the second magnetic hybrid AMR/PHR sensor, and configured to determine the difference voltage between an amplified differential voltage detected at the voltage terminals of the first magnetic sensor and an amplified differential voltage detected at the voltage terminals of the second magnetic sensor;

a set of at least one magnetic particles deposited on the active surface of the first magnetic sensor;

a processing unit for detecting from a set of different measured differential voltages output by first voltage measurement device a magnetic flux shift representative of the presence of a least one magnetic particle deposited on the first magnetic sensor;

a magnetic field generator configured to create a magnetic excitation field $H_{AC}$ to make produce by each magnetic particle a stray magnetic field, the magnetic excitation field $H_{AC}$ oscillating along the time at a constant frequency $\omega$ ranging from 10 to 3 KHz; and in that the magnetic particles or the magnetic object to be detected are motionless and placed only close to or in contact with the active surface of the first magnetic track; and the current I injected by the first current or voltage source passing through the current terminals is a direct current (DC), or an alternating current (AC), or a sum of a direct and an alternating current.

10. Micromagnetometry system according to claim 9, wherein no magnetic particles or magnetic object in nano or micro scale are deposited on the second sensor, and the processing unit is configured to after deposit of an unknown amount of magnetic particles or a magnetic object upon the first magnetic sensor, either under known predetermined physical conditions, to detect the presence of magnetic particles or a magnetic object when a second difference as the difference between a first difference and a reference difference has an amplitude greater than a predetermined detection threshold, the reference difference being the difference between a first voltage measurement carried out by the first sensor that has no magnetic particles thereon and a second voltage measurement carried out by the second sensor that has no magnetic particles thereon under the same known predetermined physical conditions, the first difference being determined by the first voltage measurement device as the difference between the first voltage measurement carried out by the first sensor that has magnetic particles thereon and the second voltage measurement carried out by the second sensor that has no magnetic particles thereon, and the predetermined detection threshold corresponding to a minimal magnetization field shift detectable of 10 nT, or when the magnetic particles are molecular nanoparticles or a magnetic object switchable by overstepping a predetermined switching threshold in terms of a switching physical property that operates as a switching command, under known predetermined physical conditions, by varying the physical property magnitude over a predetermined range of the physical property, to determine a curve as the evolution versus the physical property magnitude of the difference between a first set of differential voltage measurements and a second set of voltage measurements, the first set of voltage measurements being carried out by the first sensor that has magnetic particles thereon and the second set of voltage measurements carried out by the second sensor that has no magnetic particles thereon, and then to detect the presence of magnetic particles or magnetic object when the curve exhibits a switching physical property interval over which a transition occurs having an amplitude greater than the predetermined detection threshold, the predetermined detection threshold corresponding to a minimal magnetization field shift detectable of 10 nT.

11. Micromagnetometry system according to claim 1, wherein the magnetic particles are selected from the group consisting of:
   a switchable molecular nanoparticles in form of $A_hB_k[M(CN)_6]_1 \cdot mH_2O$, where A, B and M are transition metals and C is an alkali metal cation;
   a paramagnetic particle;
   a ferromagnetic particle;
   an antiferromagnetic particle with multilayer structure Ti/Fe, Cr, NiO, $Co_3O_4$, $a-Fe_2O_3$, CuO, MnO, $Cr_2O_3$ nanoparticles; and
   a magnetic bead made of $Fe_3O_4$ in the polymer matrix with the sphere shape and any size ranging from 50 nm to 10 μm.

12. Micromagnetometry detection method for detecting the presence of very small quantities of magnetic particles carried out by a micromagnetometry system as defined by claim 1, comprising the following steps of
   firstly, calibrating in temperature under first known predetermined physical conditions the first magnetic sensor when the system comprises a single first magnetic sensor, or the set of the first and second magnetic sensor when the magnetometry system comprises a first magnetic sensor and a second magnetic sensor by providing a first calibration background thermal noise curve; then
   depositing an unknown amount of magnetic particles upon the first magnetic sensor; then,
   under the same first known predetermined physical conditions, by varying temperature on a predetermined range of temperature,
   when the magnetometry system comprises a first single magnetic sensor, outputting a second curve as the evolution of differential voltage measurements carried out by the first sensor versus temperature, or
   when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a second curve as the evolution versus temperature of the difference between the first set of differential voltage measurements and the second set of differential voltage measurements;
   determining a third curve as the difference versus temperature between the differential voltages of the second curve and the differential voltages of the first curve within the same range of temperature; and
   detecting the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

13. Micromagnetometry detection method for detecting the presence of very small quantities of magnetic particles carried out by a micromagnetometry system as defined by claim 1, comprising the following steps of
   depositing an unknown amount of magnetic particles upon the first magnetic sensor, the magnetic particles being switchable molecular nanoparticles by overstepping a predetermined switching threshold in terms of a switching physical property that operates as a switching command, then
   in a next step, under known predetermined physical conditions, by varying the physical property magnitude over a predetermined range of the physical property,
   when the magnetometry system comprises a first single magnetic sensor, outputting a first curve as the evolution of differential voltage measurements carried out by the first sensor versus the magnitude of the physical property, or
   when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a first curve as the evolution versus the physical property of the difference between the first set of differential voltage measurements and the second set of differential voltage measurements; then
   determining over the predetermined range of the physical property a second curve as a fitting curve from a lower portion of the first curve, this lower portion of the first curve corresponding to a lower interval included within the predetermined range of the physical property having its upper bound lower than the predetermined switching threshold;
   determining a third curve as the difference versus the magnitude of the switching physical property between the differential voltages of the first curve and the differential voltages of the second curve within the same range of magnitude of the physical property; and
   detecting the presence of magnetic particles when the third curve exhibits a switching physical property interval over which a transition occurs having an amplitude greater than the predetermined detection threshold, the predetermined detection threshold corresponding to a minimal magnetization field shift detectable of 10 nT.

14. Micromagnetometry detection method according to claim 13, wherein the switching physical property is temperature, pressure, optical irradiation, electrical field, magnetic field, chemical guest molecules.

15. Micromagnetometry detection method for detecting the presence of very small quantities of magnetic particles down to a single magnetic particle or a single magnetic object in nano or micro scale carried out by a micromagnetometry system as defined in the claim 9, comprising the following steps of depositing an unknown amount of magnetic particles or a single magnetic object upon the first magnetic sensor, then either under known predetermined physical conditions, outputting a first voltage measurement carried out by the first sensor that has magnetic particles thereon and a second voltage measurement carried out by the second sensor that has no magnetic particles thereon, and determining a first difference between the first voltage measurement and the second voltage measurement; then detecting the presence of magnetic particles or a magnetic object when a second difference as the difference between the first difference and a reference difference has an amplitude greater than a predetermined detection threshold, the reference difference being the difference between a first voltage measurement carried out by the first sensor that has no magnetic particles thereon and a second voltage measurement carried out by the second sensor that has no magnetic particles thereon under the same known predetermined physical conditions, and the predetermined detection threshold corresponding to a minimal magnetization field shift detectable of 10 nT, or when the magnetic particles are molecular nanoparticles or a single object switchable by overstepping a predetermined switching threshold in terms of a switching physical property that operates as a switching command, under known predetermined physical conditions, by varying the physical property magnitude over a predetermined range of the physical property, then outputting a first set of voltage measurements carried out by the first sensor that has magnetic particles thereon and a second set of voltage measurements carried out by the second sensor that has no magnetic particles thereon, and determining a curve as the evolution versus the physical property magnitude of the difference between the first set of differential voltage measurements and the second set of voltage measurements; then detecting the presence of magnetic particles or magnetic object when the curve exhibits a switching physical property interval over which a transition occurs having an amplitude greater than the predetermined detection threshold, the predetermined detection threshold corresponding to a minimal magnetization field shift detectable of 10 nT.

16. Humidity or gas sensing measurement system comprising a micromagnetometry system as defined in claim 1, wherein the particles are molecular nanoparticles are switchable by overstepping a predetermined temperature switching threshold, the predetermined temperature switching threshold depending on the humidity of the degree environment, or on the environment concentration of any vapour of external molecules, and wherein the processing unit is configured to determine the humidity degree or the environment concentration of the vapour of external molecules from magnetic field change measurements of magnetic particles that are sensitive to the humidity degree or the environment concentration of the vapour of external molecules, and from a previously determined mapping curve between a calibrated humidity degree or a calibrated environment concentration of the vapour of external molecules measured by another method and a corresponding parameter such as a temperature threshold, a transition temperature, or a width of an hysterisis loop determined through the magnetic property change of the magnetic particles detected by the micromagnetometry method comprising the following steps of firstly, calibrating in temperature under first known predetermined physical conditions the first magnetic sensor when the system comprises a single first magnetic sensor, or the set of the first and second magnetic sensor when the magnetometry system comprises a first magnetic sensor and a second magnetic sensor by providing a first calibration background thermal noise curve; then depositing an unknown amount of magnetic particles upon the first magnetic sensor; then, under the same first known predetermined physical conditions, by varying temperature on a predetermined range of temperature, when the magnetometry system comprises a first single magnetic sensor, outputting a second curve as the evolution of differential voltage measurements carried out by the first sensor versus temperature, or when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a second curve as the evolution versus temperature of the difference between the first set of differential voltage measurements and the second set of differential voltage measurements;

determining a third curve as the difference versus temperature between the differential voltages of the second curve and the differential voltages of the first curve within the same range of temperature; and detecting the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

17. Humidity or gas sensing measurement system according to claim 16, wherein the vapour of external molecules that can be detected are amongst the external molecules selected from the group consisting of $N_2$, He, $I_2$, $CO_2$, ethanol, methanol, 2 propanol, acetone, $D_2O$, $CS_2$, CO, Iode (I), brome (Br), chlore (Cl), benzene, toluene, chlorobenzene, bromobenzene, iodobenzene, dichlorobenzene, trichlorobenzene, pyrazine, pyridine, pyrrole, thiophene, furane and thf.

18. The Micromagnetometry system according to claim 6, wherein the axis of magnetic sensor bias field $H_{DC}$ is in the range from 15 degrees to 25 degrees.

19. The Micromagnetometry system according to claim 7, wherein the current or voltage source is configured to generate an alternating current (AC) oscillating along the with time at a constant frequency ω ranging from 50 Hz to 150 Hz.

20. The micromagnetomoetry system according to claim 11, wherein:
- A is selected from the group consisting of Co, Ni and Fe;
- B is selected from the group consisting of $Fe^{II}$, $Fe^{III}$, $Mn^{II}$, $Mn^{III}$, fml a$Co^{II}$, $Co^{III}$,
- M is selected from the group consisting of $Fe^{II}$, $Fe^{III}$, $Mn^{II}$, $Mn^{III}$, fml a$Co^{II}$, $Co^{III}$;
- said paramagnetic particle is selected from the group consisting of $Fe_2O_3$, $Fe_3O_4$, Fe@$Fe_3O_4$, CoFe@$Fe_3O_4$ and Ni; and/or
- said ferromagnetic particle is selected from the group consisting of Fe, CoFe and Ni.

21. Micromagnetometry system according to claim 9, wherein the magnetic particles are selected from the group consisting of:
- a switchable molecular nanoparticles in form of $A_hB_k[M(CN)_6]_1 \cdot mH_2O$, where A, B and M are transition metals and C is an alkali metal cation;
- a paramagnetic particle;
- a ferromagnetic particle;
- an antiferromagnetic particle with multilayer structure Ti/Fe, Cr, NiO, $Co_3O_4$, a$Fe_2O_3$, CuO, MnO, $Cr_2O_3$ nanoparticles; and
- a magnetic bead made of $Fe_3O_4$ in the polymer matrix with the sphere shape and any size ranging from 50 nm to 10 µm.

22. Micromagnetometry detection method for detecting the presence of very small quantities of magnetic particles carried out by a micromagnetometry system as defined by claim 9, comprising the following steps of
- firstly, calibrating in temperature under first known predetermined physical conditions the first magnetic sensor when the system comprises a single first magnetic sensor, or the set of the first and second magnetic sensor when the magnetometry system comprises a first magnetic sensor and a second magnetic sensor by providing a first calibration background thermal noise curve; then
- depositing an unknown amount of magnetic particles upon the first magnetic sensor; then,
- under the same first known predetermined physical conditions, by varying temperature on a predetermined range of temperature,
- when the magnetometry system comprises a first single magnetic sensor, outputting a second curve as the evolution of differential voltage measurements carried out by the first sensor versus temperature, or
- when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a second curve as the evolution versus temperature of the difference between the first set of differential voltage measurements and the second set of differential voltage measurements;
- determining a third curve as the difference versus temperature between the differential voltages of the second curve and the differential voltages of the first curve within the same range of temperature; and
- detecting the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

23. Micromagnetometry detection method for detecting the presence of very small quantities of magnetic particles carried out by a micromagnetometry system as defined by claim 9, comprising the following steps of
- depositing an unknown amount of magnetic particles upon the first magnetic sensor, the magnetic particles being switchable molecular nanoparticles by overstepping a predetermined switching threshold in terms of a switching physical property that operates as a switching command, then in a next step, under known predetermined physical conditions, by varying the physical property magnitude over a predetermined range of the physical property,
- when the magnetometry system comprises a first single magnetic sensor, outputting a first curve as the evolution of differential voltage measurements carried out by the first sensor versus the magnitude of the physical property, or
- when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a first curve as the evolution versus the physical property of the difference between the first set of differential voltage measurements and the second set of differential voltage measurements; then
- determining over the predetermined range of the physical property a second curve as a fitting curve from a lower portion of the first curve, this lower portion of the first curve corresponding to a lower interval included within the predetermined range of the physical property having its upper bound lower than the predetermined switching threshold;
- determining a third curve as the difference versus the magnitude of the switching physical property between the differential voltages of the first curve and the differential voltages of the second curve within the same range of magnitude of the physical property; and
- detecting the presence of magnetic particles when the third curve exhibits a switching physical property interval over which a transition occurs having an amplitude greater than the predetermined detection threshold, the predetermined detection threshold corresponding to a minimal magnetization field shift detectable of 10 nT.

24. Micromagnetometry detection method according to claim 23, wherein the switching physical property is temperature, pressure, optical irradiation, electrical field, magnetic field, chemical guest molecules.

25. Humidity or gas sensing measurement system comprising a micromagnetometry system as defined in claim 9, wherein the particles are molecular nanoparticles are switchable by overstepping a predetermined temperature switching threshold, the predetermined temperature switching threshold depending on the humidity of the degree environment, or on the environment concentration of any vapour of external molecules, and wherein the processing unit is configured to determine the humidity degree or the environment concentration of the vapour of external molecules from magnetic field change measurements of magnetic particles that are sensitive to the humidity degree or the environment concentration of the vapour of external molecules, and from a previously determined mapping curve between a calibrated humidity degree or a calibrated environment concentration of the vapour of external molecules measured by another method and a corresponding parameter such as a temperature threshold, a transition temperature, or a width of an hysterisis loop determined through the magnetic property change of the magnetic particles detected by the micromagnetometry method comprising the following steps of firstly, calibrating in temperature under first known predetermined physical conditions the first magnetic sensor when the system comprises a single first magnetic sensor, or the set of the first and second magnetic sensor when the magnetometry system comprises a first magnetic sensor and a second magnetic sensor by providing a first calibration background thermal noise curve; then depositing an unknown amount of magnetic particles upon the first magnetic sensor; then, under the same first known predetermined physical conditions, by varying temperature on a predetermined range of temperature, when the magnetometry system comprises a first single magnetic sensor, outputting a second curve as the evolution of differential voltage measurements carried out by the first sensor versus temperature, or when the magnetometry system comprises a first magnetic sensor and a second magnetic sensor, outputting a first set of differential voltage measurements carried out by the first sensor that has magnetic particles thereon and a second set of differential voltage measurements carried out by the second sensor that has no magnetic particles thereon, and determining a second curve as the evolution versus temperature of the difference between the first set of differential voltage measurements and the second set of differential voltage measurements;

determining a third curve as the difference versus temperature between the differential voltages of the second curve and the differential voltages of the first curve within the same range of temperature; and detecting the presence of magnetic particles when the absolute value of voltage differences of the third curve remains stable above a predetermined detection threshold or the third curve exhibits a temperature interval over which a transition occurs having an amplitude greater than the predetermined detection threshold, the predetermined detection threshold corresponding to a minimal magnetization field shift detectable of 10 nT.

26. Humidity or gas sensing measurement system according to claim 25, wherein the vapour of external molecules that can be detected are amongst the external molecules selected from the group consisting of $N_2$, He, $I_2$, $CO_2$, ethanol, methanol, 2propanol, acetone, $D_2O$, $CS_2$, CO, Iode (I), brome (Br), chlore (Cl), benzene, toluene, chlorobenzene, bromobenzene, iodobenzene, dichlorobenzene, trichlorobenzene, pyrazine, pyridine, pyrrole, thiophene, furane and thf.

27. The micromagnetomoetry system according to claim 21, wherein:

A is selected from the group consisting of Co, Ni and Fe;

B is selected from the group consisting of $Fe^{II}$, $Fe^{III}$, $Mn^{II}$, $Mn^{III}$, fml a$Co^{II}$, $Co^{III}$;

M is selected from the group consisting of $Fe^{II}$, $Fe^{III}$, $Mn^{II}$, $Mn^{III}$, fml a$Co^{II}$, $Co^{III}$;

said paramagnetic particle is selected from the group consisting of $Fe_2O_3$, $Fe_3O_4$, Fe@$Fe_3O_4$, CoFe@$Fe_3O_4$ and Ni; and/or said ferromagnetic particle is selected from the group consisting of Fe, CoFe and Ni.

* * * * *